(12) United States Patent
Toda et al.

(10) Patent No.: US 8,164,844 B2
(45) Date of Patent: Apr. 24, 2012

(54) OPTICAL FILTER AND LIGHTING APPARATUS

(75) Inventors: Naohiro Toda, Osaka (JP); Wataru Tanaka, Osaka (JP); Hiroki Noguti, Osaka (JP)

(73) Assignee: Panasonic Corporation, Osaka (JP)

( * ) Notice: Subject to any disclaimer, the term of this patent is extended or adjusted under 35 U.S.C. 154(b) by 357 days.

(21) Appl. No.: 11/886,335

(22) PCT Filed: Sep. 13, 2005

(86) PCT No.: PCT/IB2005/052987
§ 371 (c)(1),
(2), (4) Date: Sep. 14, 2007

(87) PCT Pub. No.: WO2006/097794
PCT Pub. Date: Sep. 21, 2006

(65) Prior Publication Data
US 2008/0266690 A1    Oct. 30, 2008

(30) Foreign Application Priority Data

Mar. 16, 2005    (JP) ................................. 2005-074796

(51) Int. Cl.
*G02B 5/22* (2006.01)
*G02B 5/28* (2006.01)
(52) U.S. Cl. ........................................ 359/885; 359/589
(58) Field of Classification Search .................. 359/885, 359/589
See application file for complete search history.

(56) References Cited

U.S. PATENT DOCUMENTS

| 4,480,894 A | 11/1984 | Miller et al. |
| 5,177,509 A | 1/1993 | Johansen et al. |
| 6,259,572 B1 * | 7/2001 | Meyer, Jr. ...................... 359/885 |
| 2002/0005509 A1 * | 1/2002 | Teng et al. ...................... 252/582 |
| 2007/0268234 A1 | 11/2007 | Wakabayashi et al. |

FOREIGN PATENT DOCUMENTS

| JP | 03-235901 A | 10/1991 |
| JP | 6-314595 A | 11/1994 |
| JP | 2000-090887 A | 3/2000 |
| JP | 2000 252084 A | 9/2000 |

(Continued)

OTHER PUBLICATIONS

Japanese Office Action corresponding to Japanese Patent Application No. 2005-074796 issued on Jul. 6, 2010. Japanese Office Action issued in corresponding Japanese Patent Application No. 2005-074796 on Jun. 28, 2011.

*Primary Examiner* — Jade R Chwasz
(74) *Attorney, Agent, or Firm* — Sughrue Mion, PLLC

(57) ABSTRACT

An optical filter and a lighting device using the same wherein the suppression of the melatonin secretion by the reception of light in the nighttime is prevented and the color of light is maintained. The optical filter has a mean transmissivity of a light beam in a wavelength range of about 480~550 nm is about 30% or less. The optical filter is formed by at least molding a transparent resin and a resin composition material containing an orange color series florescent dye material, and, for 100 weight part of the transparent resin, the resin composition material containing about 0.005~0.2 weight part of the orange color series florescent dye material is molded. This can prevent the suppression of the melatonin secretion in the nighttime. The color of light is maintained desirable. The optical filter may be applied to a lighting apparatus.

6 Claims, 15 Drawing Sheets

FOREIGN PATENT DOCUMENTS

| | | |
|---|---|---|
| JP | 2002-015462 A | 1/2002 |
| JP | 2002-030220 A | 1/2002 |
| JP | 2005 230171 A | 12/2003 |
| JP | 2004-075709 A | 3/2004 |
| JP | 2005 310654 A | 11/2005 |
| WO | WO 2004/021071 A | 3/2004 |
| WO | 2004/088616 A1 | 10/2004 |
| WO | 2005/004948 A2 | 6/2011 |

* cited by examiner

[Fig. 1]
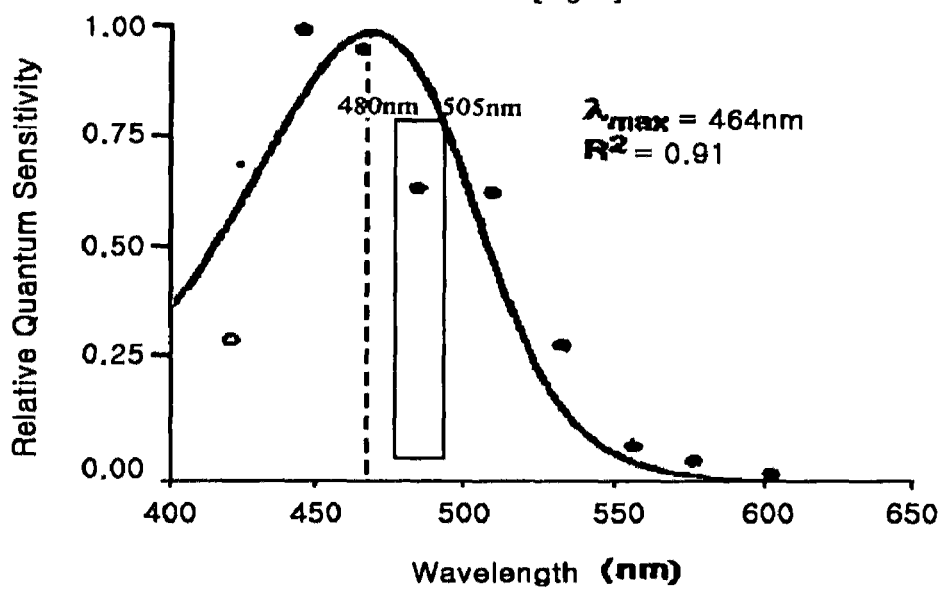
[Fig. 2]
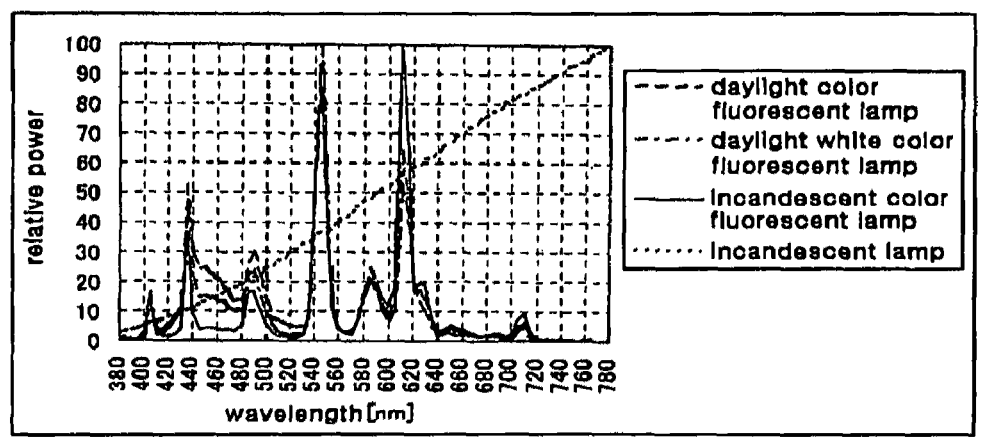

[Fig. 3]
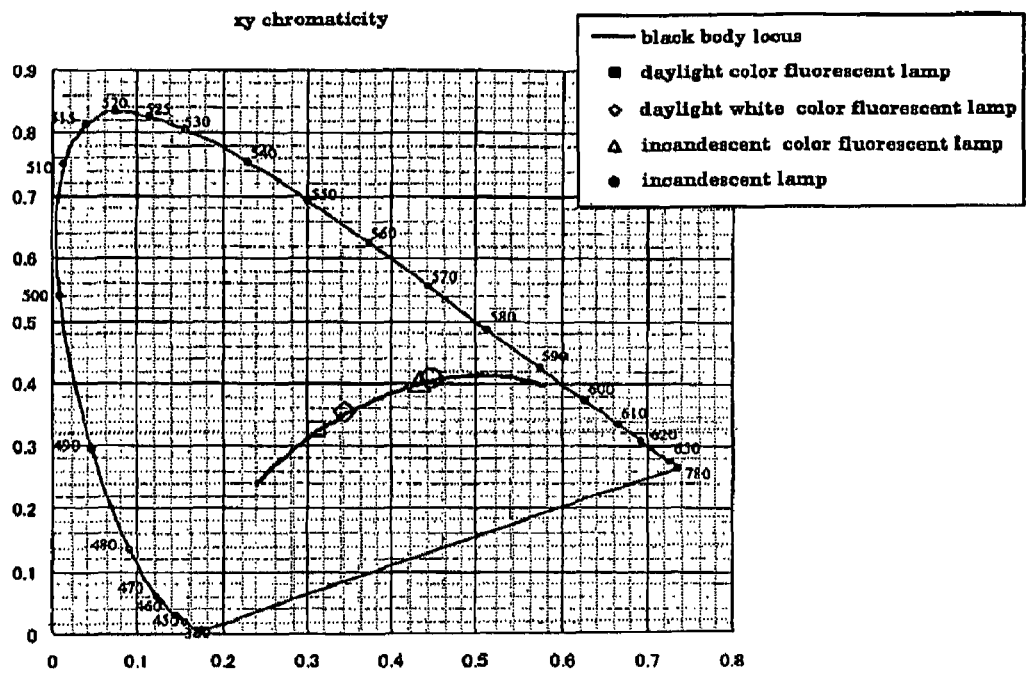
[Fig. 4]
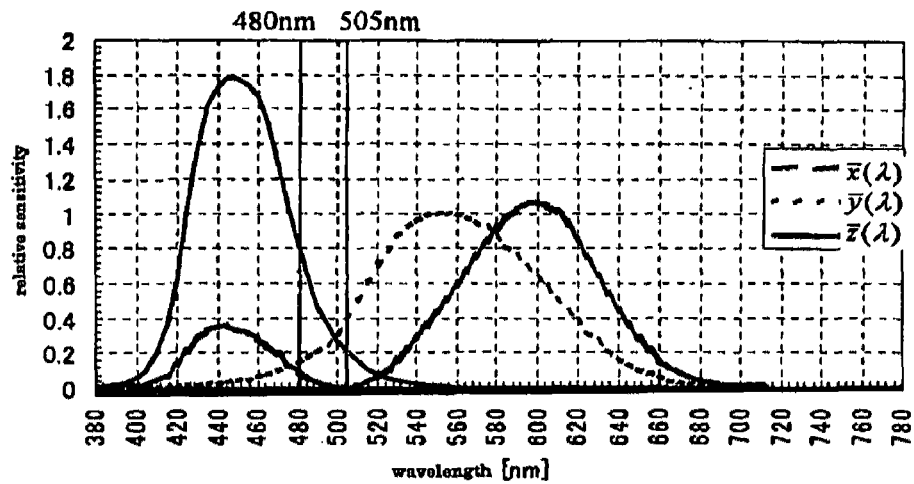

[Fig. 5]
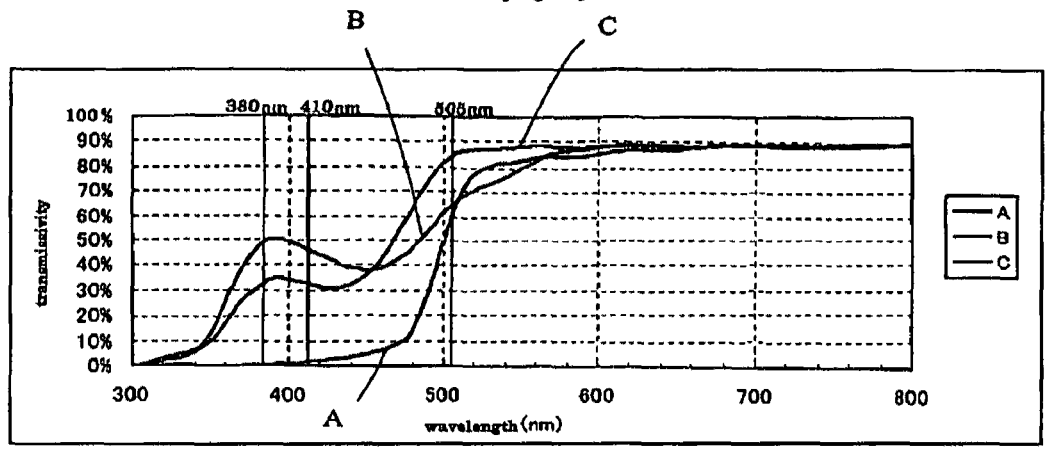
[Fig. 6]
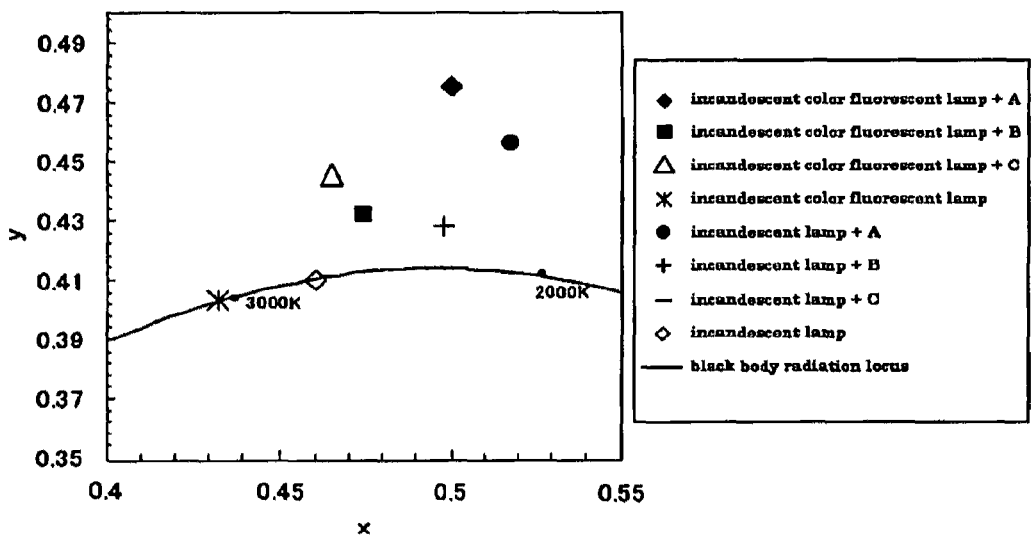
[Fig. 7]
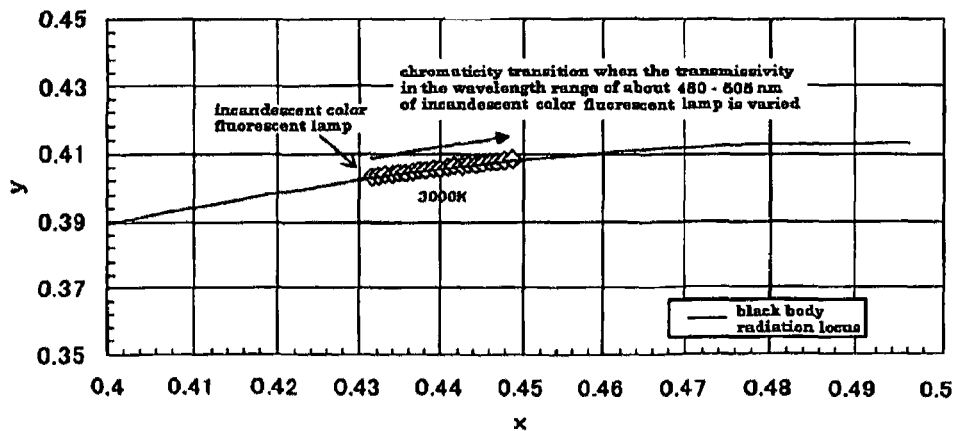

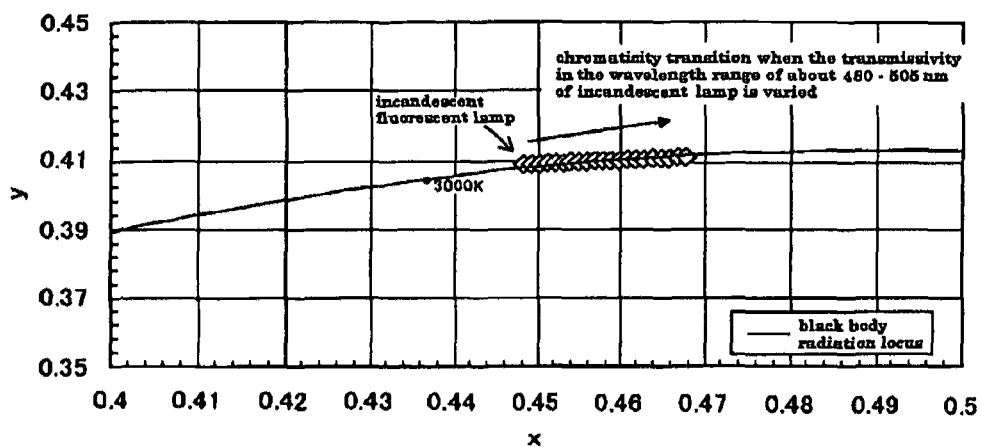
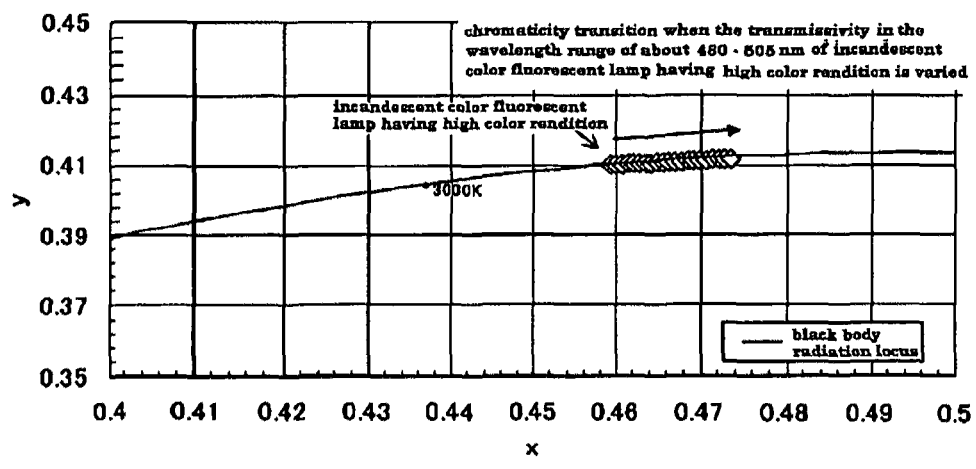
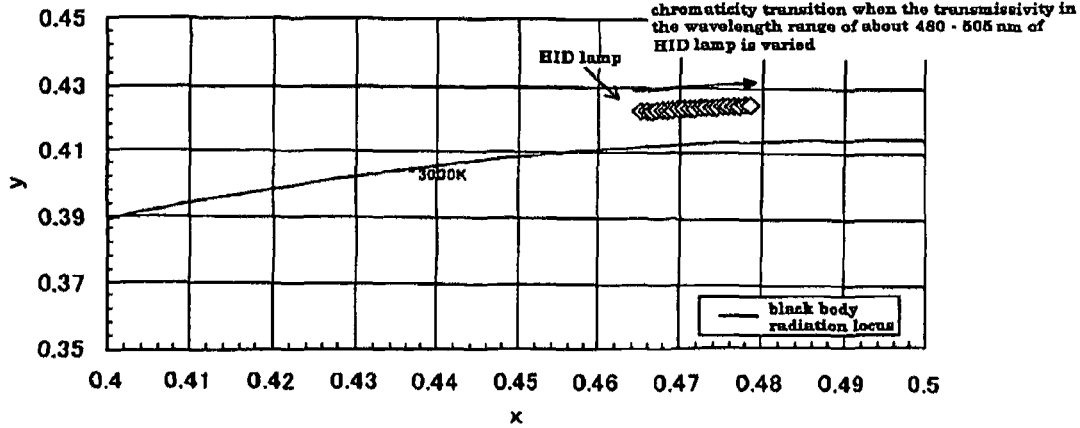

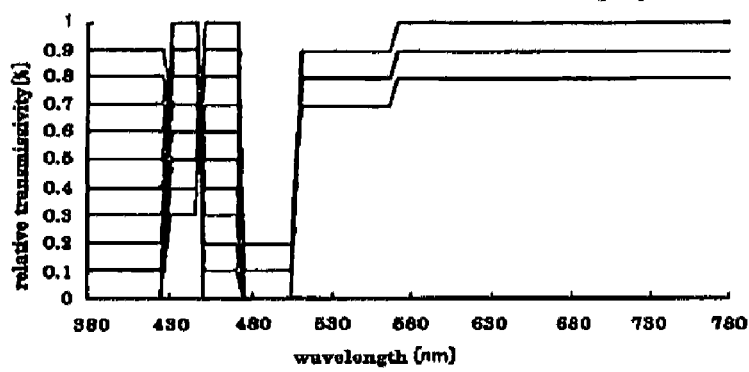
[Fig. 11]
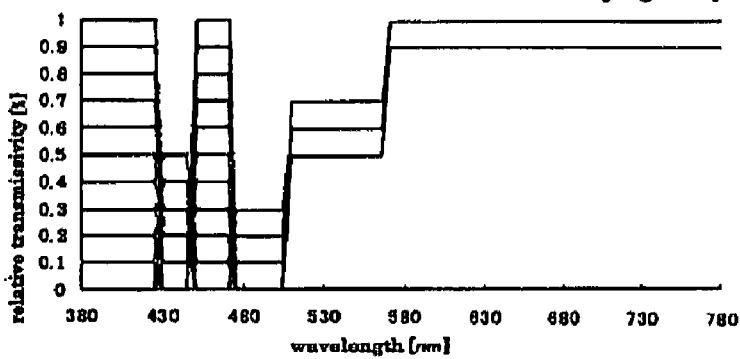
[Fig. 12]
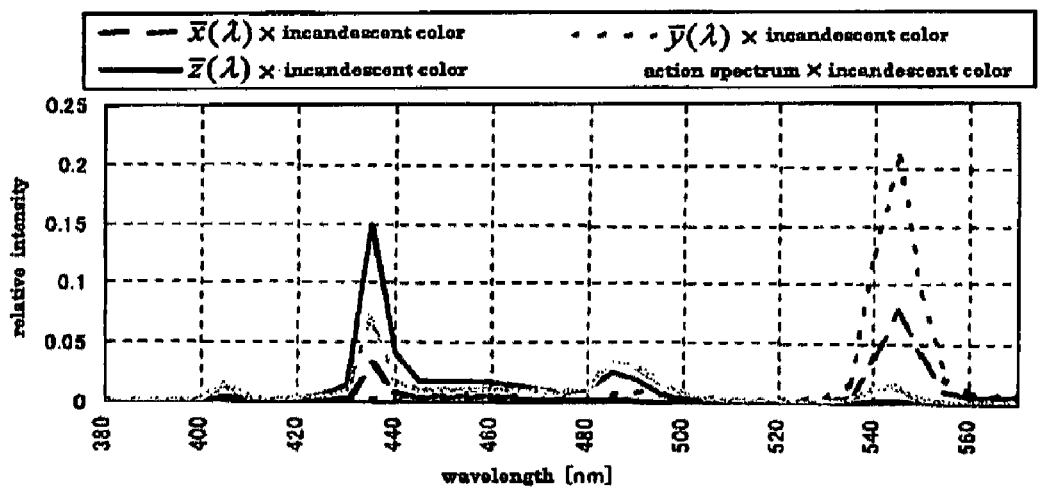
[Fig. 13]

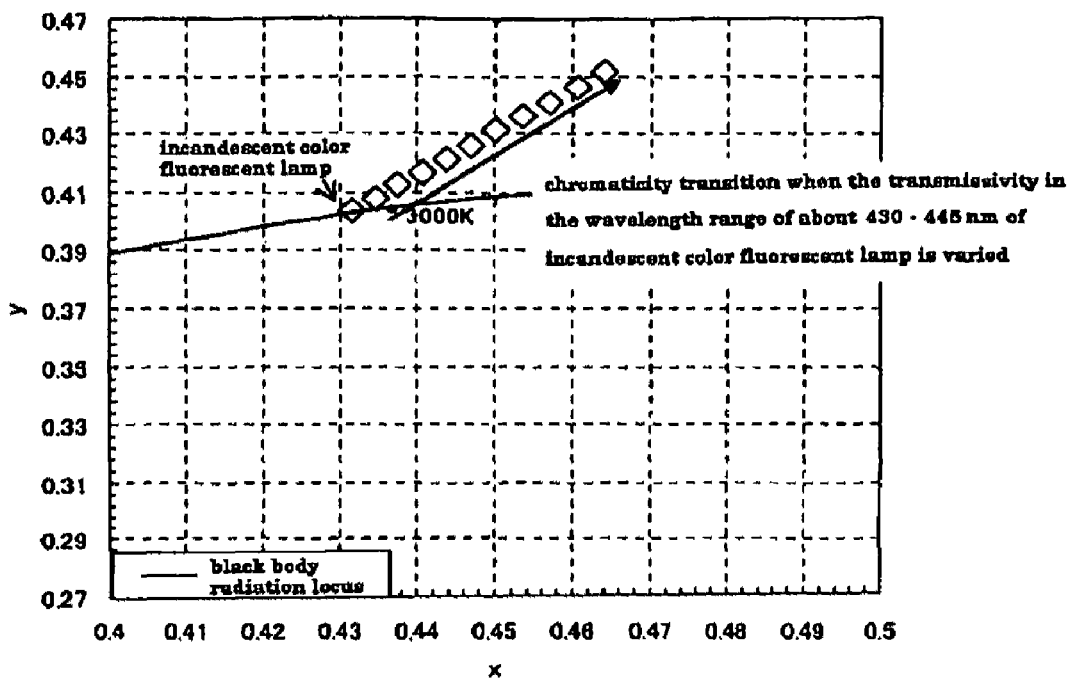
[Fig. 14]
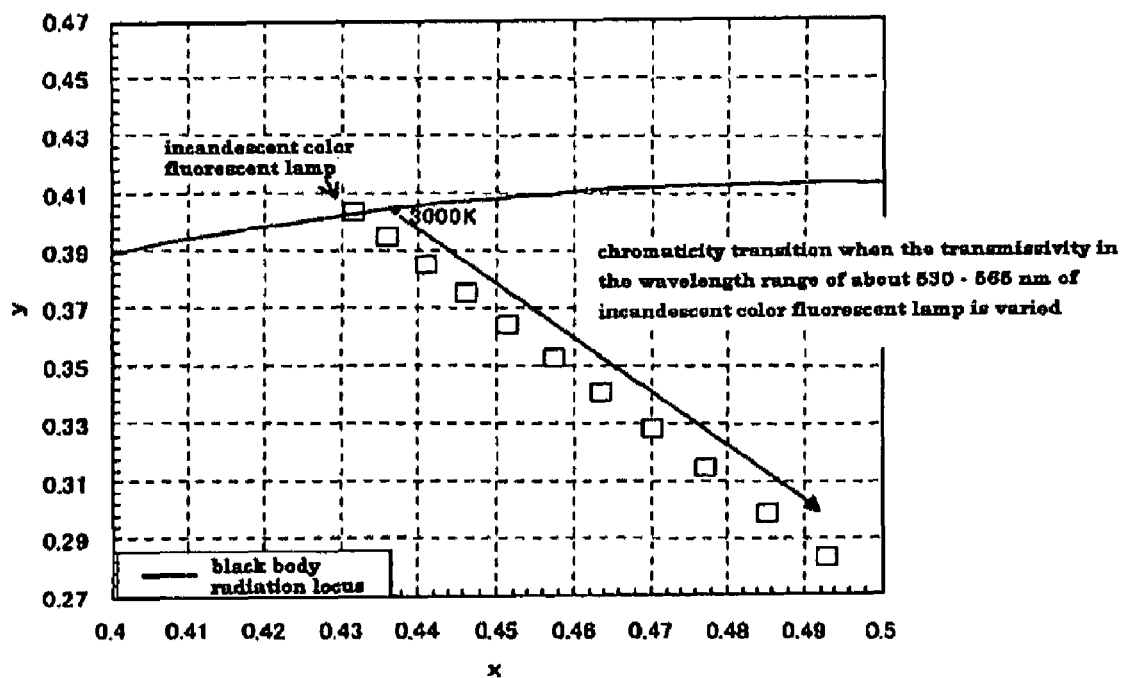
[Fig. 15]

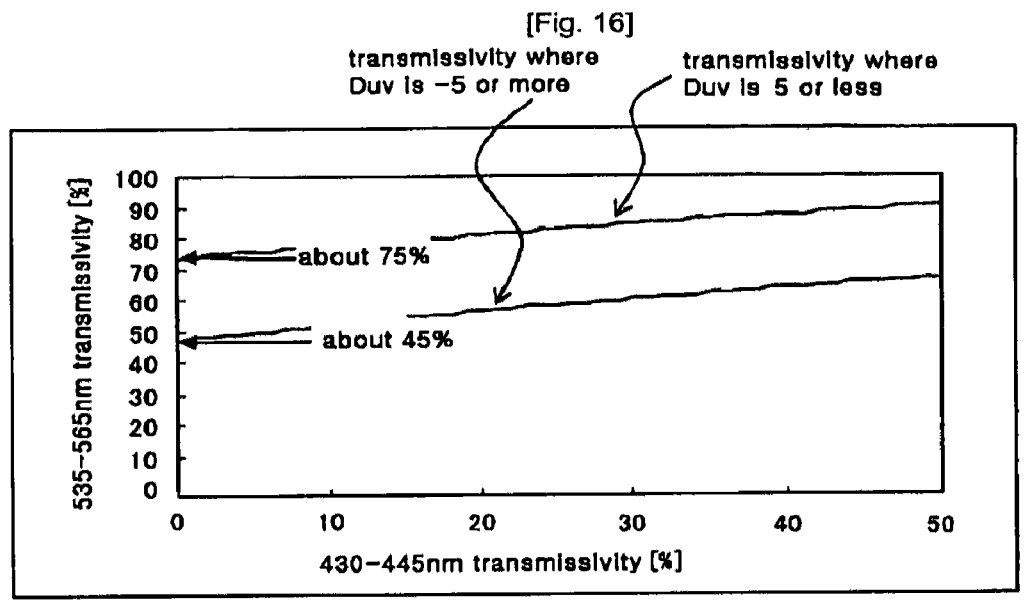
[Fig. 16]
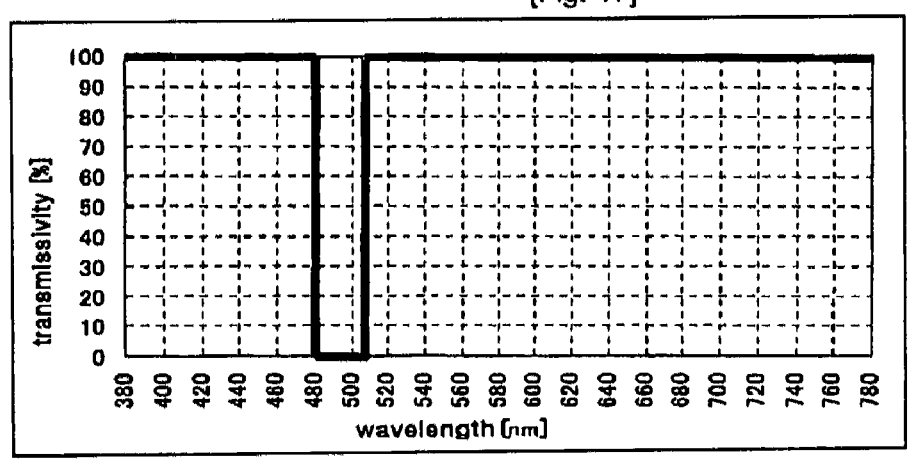
[Fig. 17]
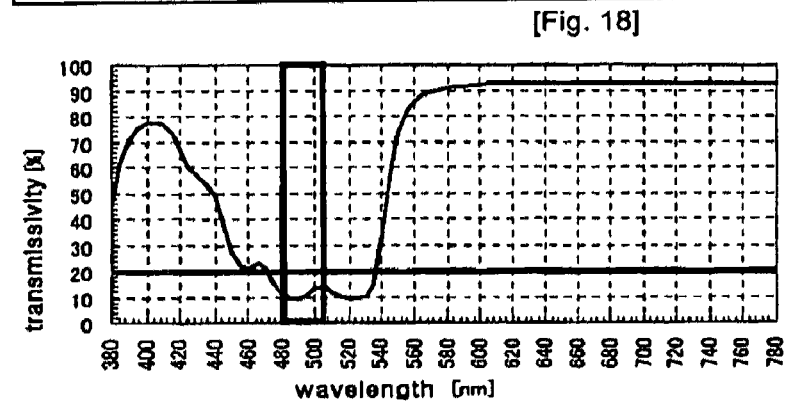
[Fig. 18]

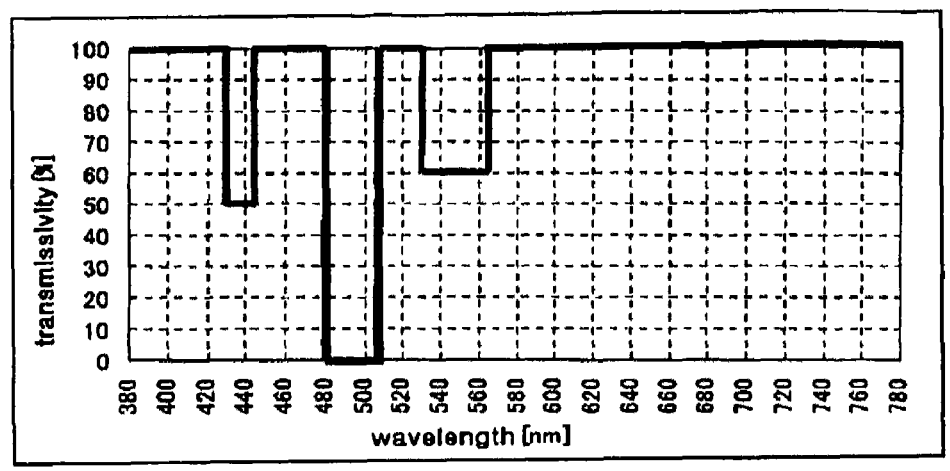
[Fig. 19]
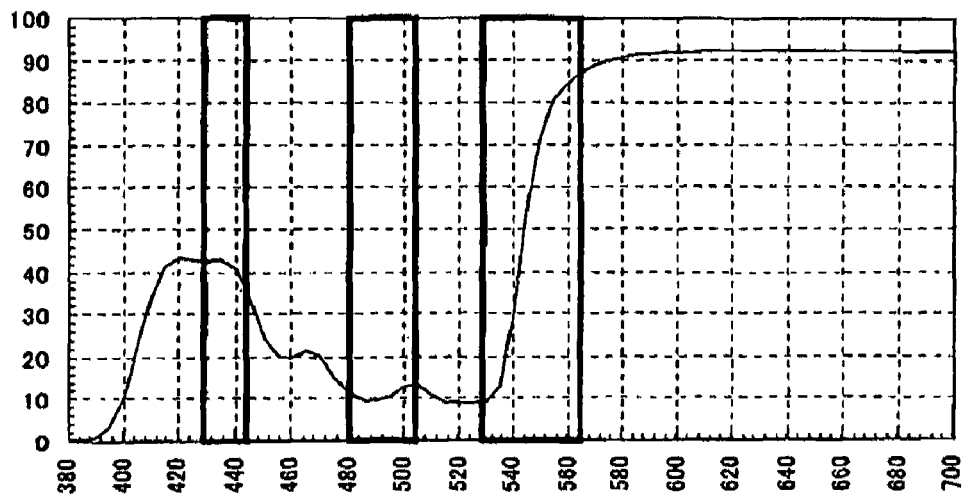
[Fig. 20]

[Fig. 21]
[A]
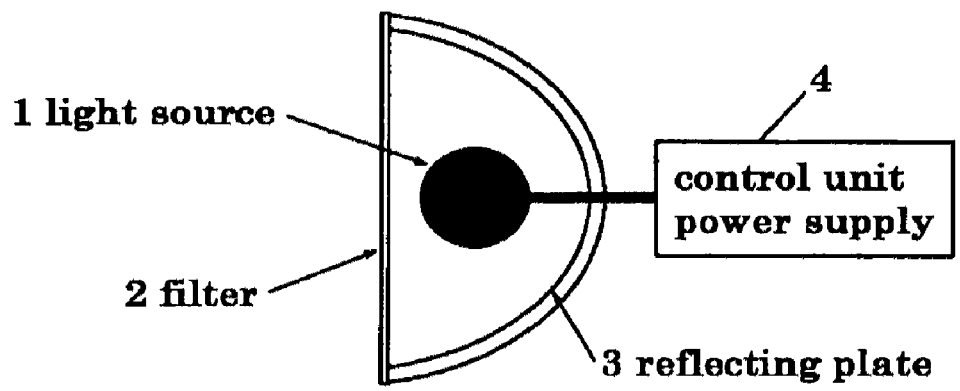
[B-1]        [B-2]
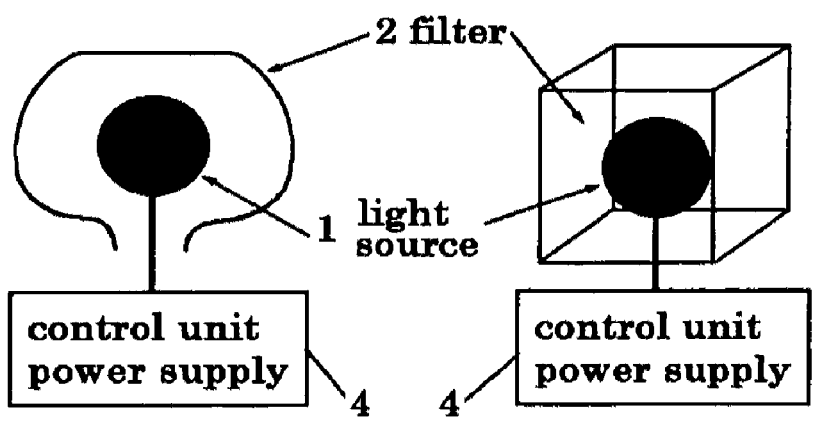

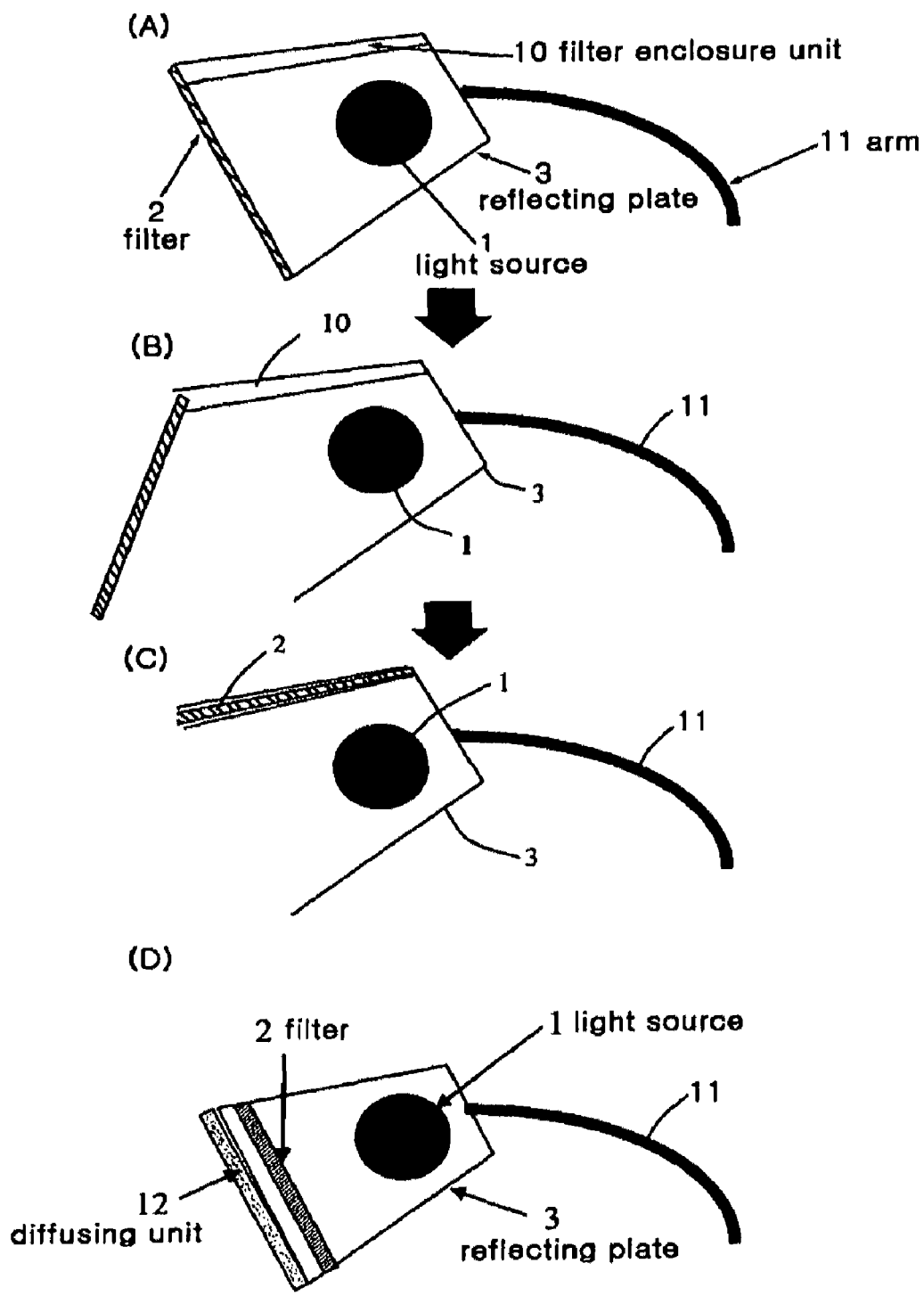

[Fig. 23]
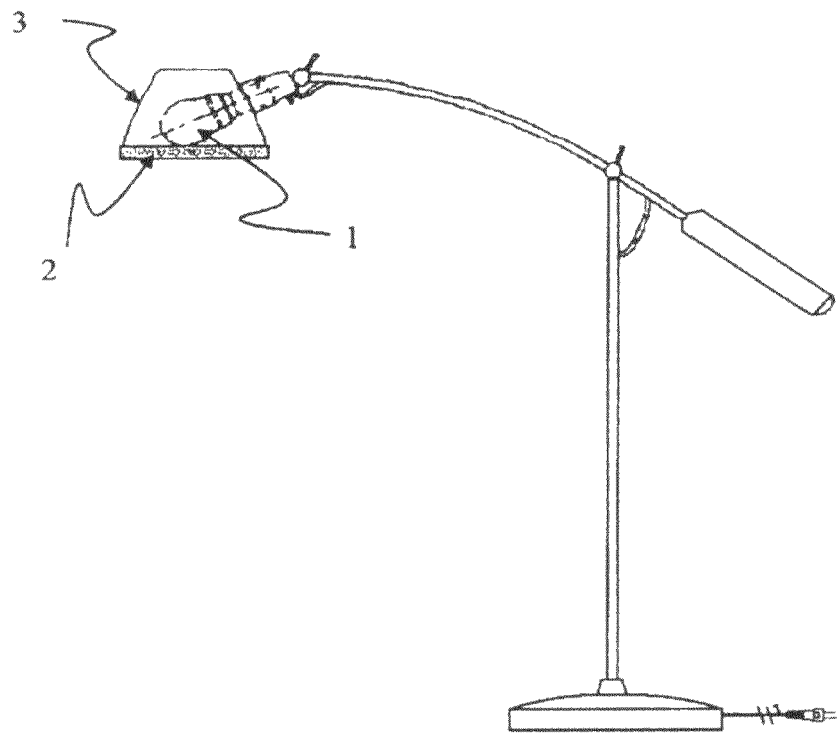
[Fig. 24]
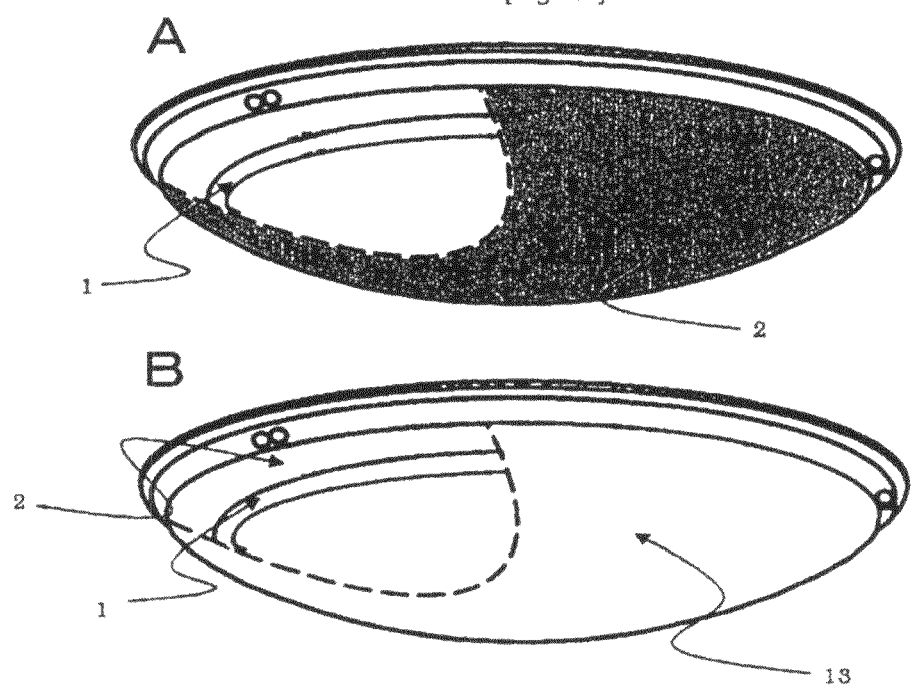

[Fig. 25]
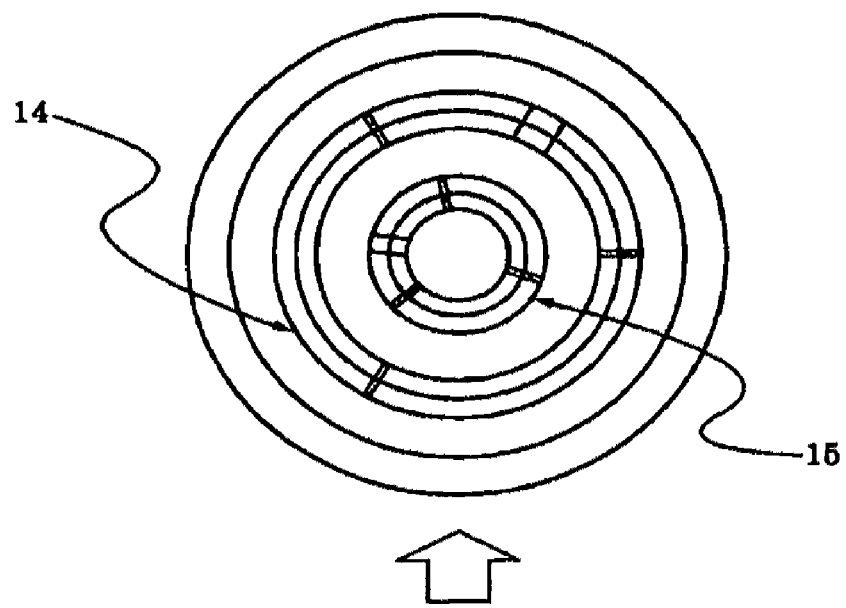
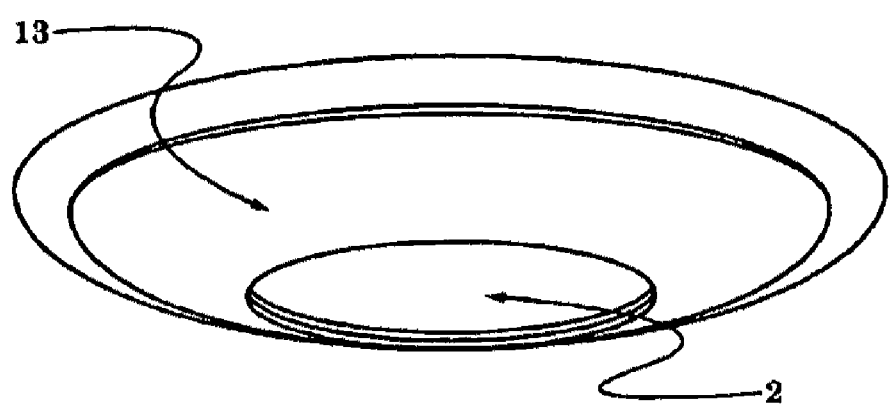
[Fig. 26]
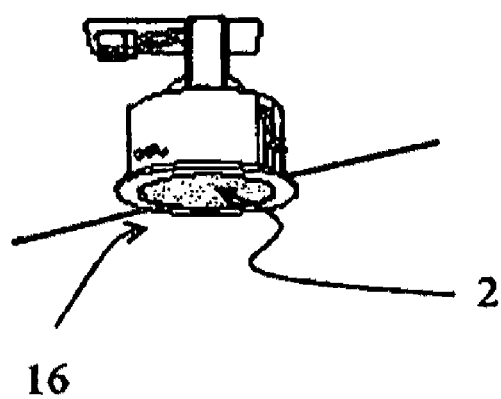

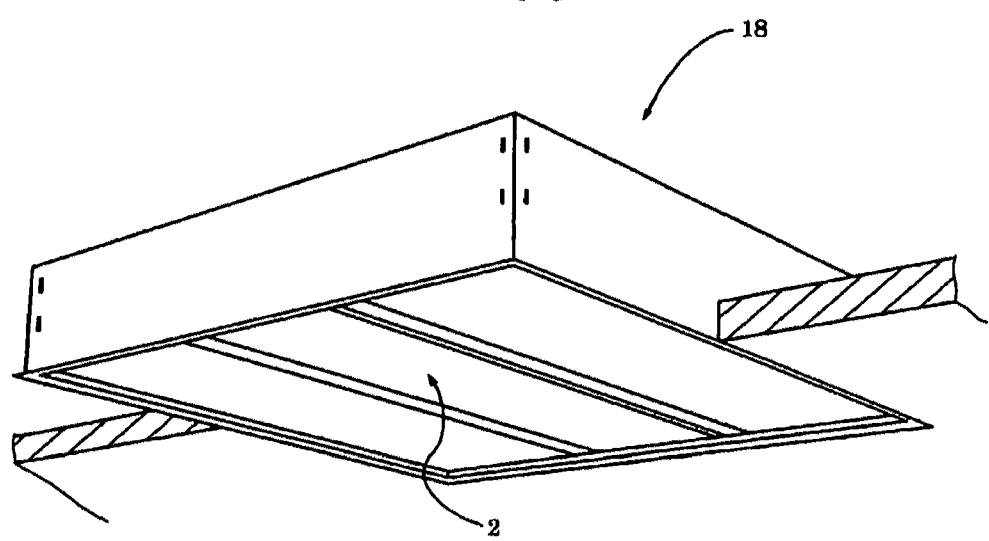
[Fig. 27]

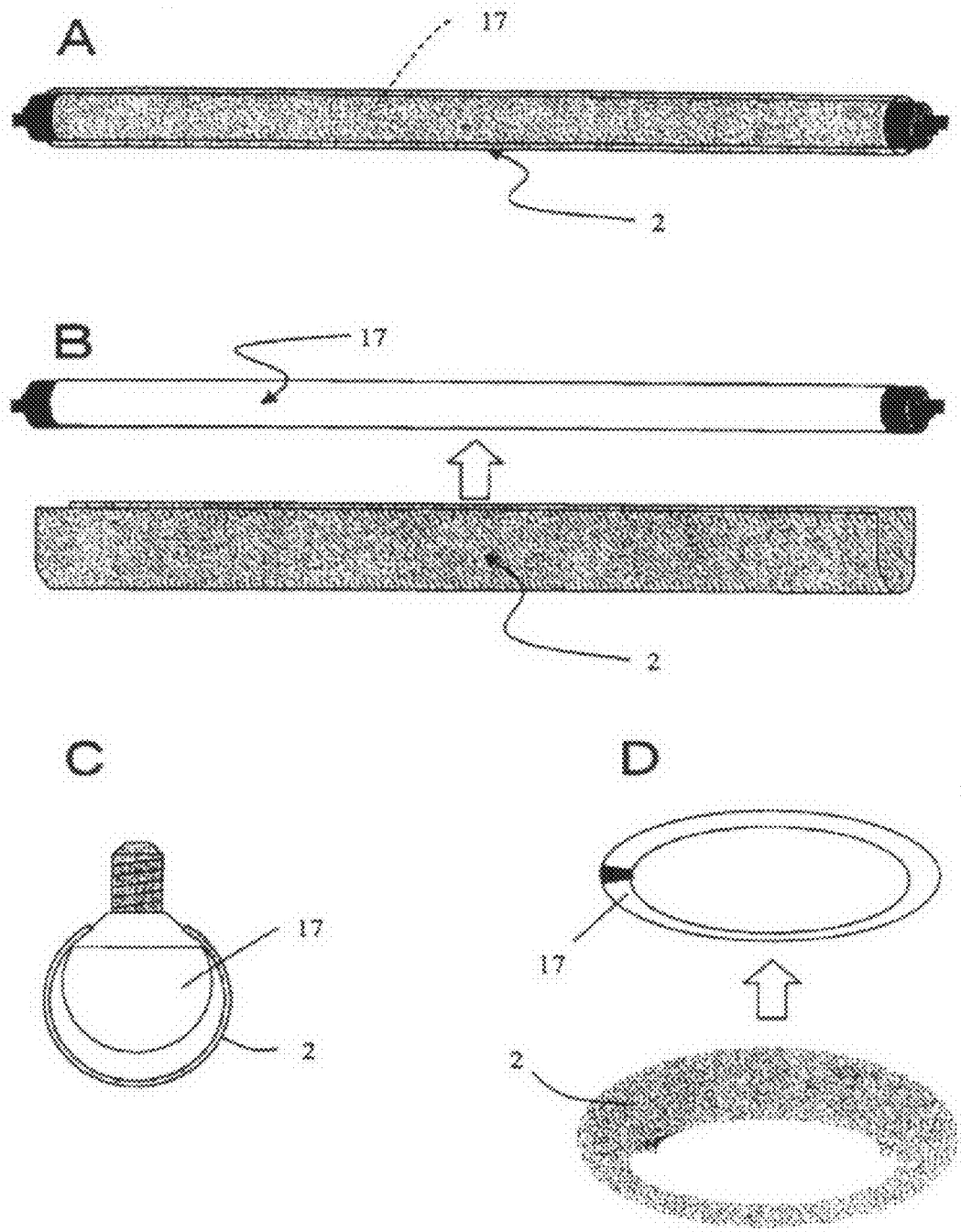
[Fig. 28]

[Fig. 29]
(a)
(b)
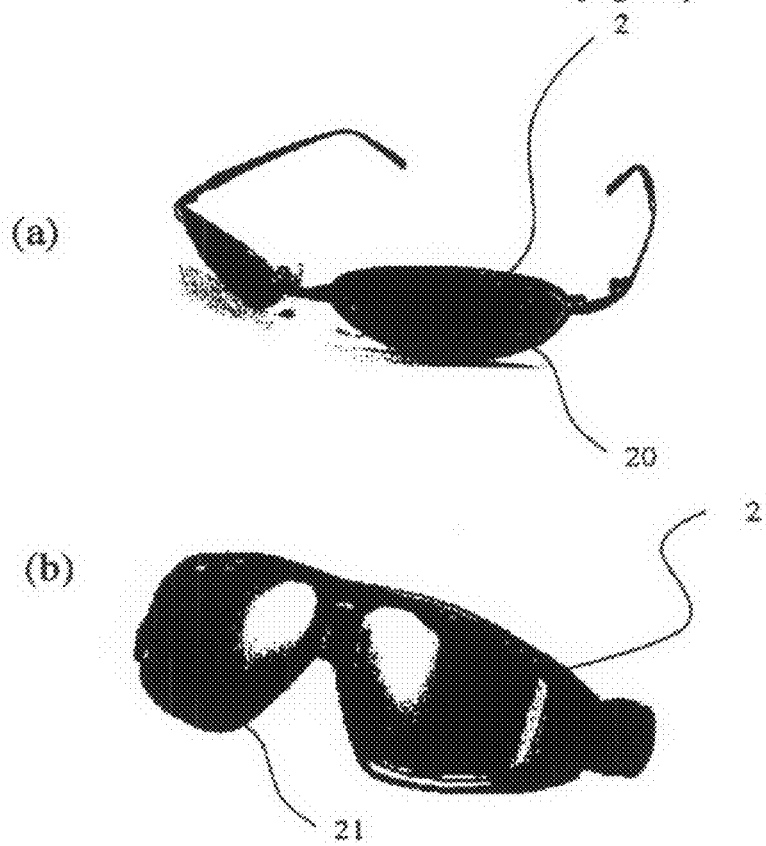
[Fig. 30]
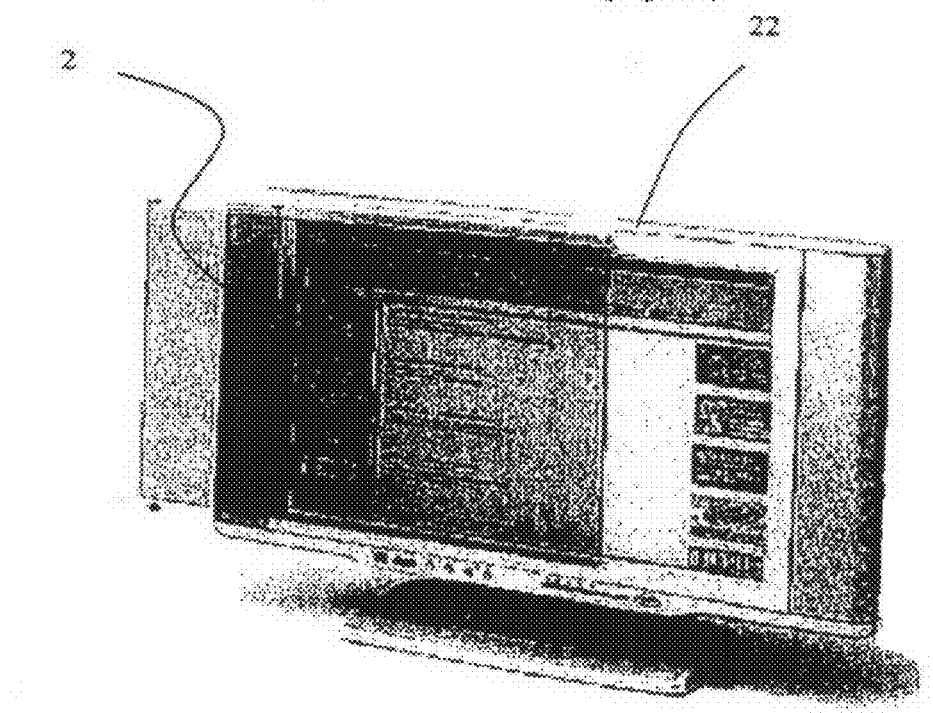

OPTICAL FILTER AND LIGHTING APPARATUS

TECHNICAL FIELD

The present invention relates to an optical filter and a lighting apparatus using the same.

BACKGROUND ART

Conventionally, during nighttime, especially prior to bedtime, it is known that a stimulation of an encephalon is reduced by configuring a color temperature of a lighting in a living space to a lower color temperature (reddish color light such as a light bulb) when compared to using a white color light and a daylight color light and that a smooth sleep is facilitated by. A technology for varying a color of light according to time or a person's biorhythm has been proposed (for example, see patent reference 1).

With respect to the above, a novel idea regarding a relation between a wavelength of a light and a biorhythm and a sleep is reported in a paper of non-patent reference 1.

In accordance with the non-patent reference 1, a wavelength characteristic of a suppression of the melatonin secretion by a reception of light in the nighttime is disclosed. Melatonin is a hormone secreted from a pineal gland in the encephalon and is secreted from prior to sleep to the entire sleep time (from 10 P.M. to late night although dependent upon individual or biorhythm). It is known to stimulate a body temperature drop or a sleep.

The melatonin is known as what its secretion is suppressed by the reception of the light in the nighttime, and an action spectrum representing the wavelength characteristic as shown in FIG. 1 is disclosed in the paper. As shown in FIG. 1, the wavelength where a sensitivity of the suppression of the melatonin secretion is at its peak is 464 nm, and the suppression of the melatonin secretion is prevented by maximally blocking a neighboring wavelength component close to the wavelength of 464 nm.

In addition, as shown in spectral distributions of various light sources in FIG. 2, the wavelength component exists in a light source having a low color temperature, an incandescent lamp or an incandescent color fluorescent lamp generally used in an indoor lighting space although it is small in amount when compared to a white color or an daylight color fluorescent lamp. Therefore, this induces the suppression of the melatonin secretion (see non-patent reference 2).

Based on the above-described idea, a technology regarding a lighting apparatus and a light source for use with the same has been developed for embodying security of visual information without hindering sleep due to the suppression of the melatonin secretion by the reception of light in the nighttime (by way of an example, see patent reference 2). In accordance with the patent reference 2, blocking or attenuating a light of a wavelength of about 410~505 nm which has a high suppression effect of the melatonin secretion in the nighttime has been proposed. Moreover, by adding or passing through a light of a wavelength about 400 nm, an effective way of preventing the suppression of the melatonin secretion has been proposed while maintaining a color of the light desirable.

In addition, it is known that irradiating an intense light in a broad daylight, especially in the morning, has an effect of adjusting a biorhythm. However, based on the above-described idea, by actively using a light having a center wavelength of 464 nm to the contrary, a method for effectively adjusting the biorhythm has been proposed (see patent reference 3).

As described above, in order to create a light which does not suppress the melatonin secretion, a method for blocking or attenuating a wavelength which suppresses the melatonin secretion by using an optical filter can be considered other than using a light that does not generate a wavelength which suppresses the secretion of melatonin.

[Patent reference 1] Japanese patent publication no. 2000-252084

[Patent reference 2] Japanese patent application no. 2004-041545

[Patent reference 3] Japanese patent application no. 2004-128465

[Non-patent reference 1] G. C. Brainard et al. (2001): 'Action Spectrum for Melatonin Regulation in Humans: Evidence for a Novel Circadian Photoreceptor', The Journal of Neuroscience, Aug. 15, 2001, 21(16), pp 6405-6412

[Non-patent reference 2] Sato M, Noguchi H, Morita T (2004): The Effects of Light with Different Spectral Distribution During the Nighttime on Melatonin Secretion and Psychological Factors in Humans, CIE Expert Symposium on Light and Health abstract, 87-88(Sep. 30-Oct. 2, 2004, pp 87-88)

As described above, when viewed from an aspect of melatonin stimulating the body temperature drop or the sleep in the nighttime, the reception of the light containing the wavelength range, prior to sleep in the nighttime, should be avoided for a fine quality of sleep, and should also be coped with in a level of a lighting apparatus or a light source.

DISCLOSURE OF INVENTION

Technical Problem

As described above, a configuration of a lighting space of a lower color temperature (incandescent color) has been proposed. However, even the light source having the low color temperature, the incandescent lamp or the incandescent color fluorescent lamp generally used in an indoor lighting space causes the suppression of the melatonin secretion as described above.

Ideally, it is preferable that an output in the wavelength range is set close to zero. However, a light that is output from a filament of an incandescent lamp includes the output in the wavelength range. In case of a fluorescent lamp, although an output wavelength configuration may be designed by selecting a fluorescent substance, their correspondence in a light source level, that is, a reduction of the light output in the wavelength range has its limits because a luminous peak of mercury is included in the wavelength range.

In addition, although there are light sources that have been blocked of the wavelength range, for example a low pressure sodium lamp or a red or an orange color LED, etc., these lamps have a very low color rendition so that they are not generally suitable for a light source of indoor lighting.

In order for a color to look natural as an illuminating light, firstly, a chromaticity coordinate of the illumination light is required to be on a black body radiation locus or adjacent region thereto on a chromaticity diagram. A deviation from the black body radiation locus is represented as a Duv, and it is known that when the Duv is a positive number, the light seems to be green in color, and when the Duv is a negative number, the light seems to be reddish violet in color. Ideally, it is desirable that the Duv is as small a value as possible.

Moreover, in order to be desirable as a lighting light, there is a (correlation) color temperature representing a chromaticity of the lighting, an average color rendition valuation index which is a valuation index of viewing method of color of an object lighted by the light and so on, and a desirable color as a light means that at least three of these valuation index are desirable.

That is, the natural color of light means that each wavelength component is evenly included and that the color of light is on or close to the black body radiation locus. FIG. 3 is a graph illustrating xy chromaticity and the black body radiation locus. A chromaticity coordinate graph shown in FIG. 2 is also illustrated in FIG. 3. As shown FIG. 3, a generally used light source in indoor lighting space is on or close to the black body radiation locus.

However, when a wavelength about 464 nm is to be reduced as much as possible so as to prevent the suppression of the melatonin secretion in the nighttime, a light of short wavelength which is a blue color component must be reduced, thereby destroying a balance as a natural color light. As a result, the low-pressure sodium lamp or the red or the orange color LED and the like become not suitable for the color of lighting in a living environment.

The xy chromaticity graph shown in FIG. 3 is obtained from tri-stimulus values XYZ. Every color can be represented as tri-stimulus values xyz, and the tri-stimulus values XYZ are obtained based on three isochromatic functions $x(\lambda)$, $y(\lambda)$ and $z(\lambda)$. FIG. 4 illustrates these isochromatic functions. $x(\lambda)$ approximately represents red color, $y(\lambda)$ approximately represents green color and $z(\lambda)$ approximately represents blue of the isochromatic functions. By way of an example, in order to obtain tri-stimulus value X of a certain illuminating light $S(\lambda)$, it can be obtained based on an integral value of $x(\lambda) \times S(\lambda)$ with respect to a wavelength range of a visible light. The same applies to tri-stimulus values Y and Z, and the same method applies to the action spectrum shown in FIG. 1 as the isochromatic functions.

When a light near a wavelength about 464 nm is reduced so as to prevent the suppression of the melatonin secretion, a blue chromaticity is simultaneously lost because $z(\lambda)$ of the three isochromatic functions and most of the action spectrum shown in FIG. 1 overlap each other, thereby the color of the light becoming unnatural.

Therefore, in accordance with patent reference 2 (Japanese Patent Publication 2004-041545), the color of the light is improved by blocking or attenuating a light in a wavelength range of 410~505 nm which has a relatively high suppression efficiency of the melatonin secretion, and by adding a light source emitting a light having a wavelength of about 400 nm which has a low suppression efficiency of the melatonin secretion.

However, as shown in FIGS. 1 and 4, an improvement of the color cannot be expected because not only the suppression efficiency of the melatonin secretion is low at the wavelength of about 400 nm but an efficiency of all the isochromatic functions $x(\lambda)$, $y(\lambda)$ and $z(\lambda)$ is also low. That is, on the contrary, in order that lighting looks as natural color by adding the light having a wavelength of about 400 nm, a large amount of the light having the wavelength of about 400 nm is necessary. The addition of a large amount of a light in the wavelength range, although the light has low suppression efficiency of the melatonin secretion, results in the suppression of the melatonin secretion.

The same applies when a light in the wavelength range about 410~505 nm is blocked and nearly all the lights in the wavelength range of about 380~410 nm are passed through instead of adding the light having the wavelength of about 400 nm. That is, the improvement of the color can little be expected because the light in the wavelength ranges of about 380~410 nm has low efficiency although the light is blue in color.

FIG. 5 exemplifies of a spectrum transmissivity of an optical filter for blocking or attenuating a range including a wavelength range of about 410~505 nm. FIG. 6 illustrates a chromaticity coordinate when lights of an incandescent color fluorescent lamp and an incandescent lamp of the light sources shown in FIG. 2 are passed through various optical filters shown in FIG. 5, respectively. An optical filter (B) of the optical filters in FIG. 5 has a low transmissivity in 410~505 nm range, and has a relatively high transmissivity in 380~410 nm range. However, as shown in FIG. 6, the optical filter (B) deviates from the black body radiation locus, i.e. Duv is large.

Generally, as for the types of optical filters, there is a type formed on a plate or a film using a coloring resin material, an optical multi-layer film formed on a glass material. The optical filter, which is formed by forming the optical multi-layer film formed on the glass material, can be controlled to pass or block a light having a certain wavelength by film design. However, the optical filter by the optical multi-layer film is characterized in that transmitting wavelength range is shifted by an incident angle of the light. Therefore, in case of an optical filter such as a notch optical filter for laser light, for example, it is disadvantageous in that the notch optical filter can only be used with a very narrow incident angle such as 0±0.5° and with a certain light source which is unidirectional such as the laser light. Moreover, in case of the glass material, it is disadvantageous in that the glass material can hardly be formed in an arbitrary shape compared to a resin, and a large number of manufacturing processes are required for forming the optical multi-layer film so that a manufacturing cost is high, resulting in a very limited usage.

On the other hand, in case of a type formed on a plate or a film using a coloring resin material, compared to the optical multi-layer film formed on the glass material, it is advantageous in the formation of shape and the cost. However, an embodiment of a pass/block range or a level control possible in the optical multi-layer film formed on the glass material has usually been difficult. Although a coloring component or other additives can be combined to control an optical property to a certain degree, it is very difficult to sharply block or pass a light having a multiple wavelength range.

By way of an example, although there is a transparent resin material including a fluorescent coloring material which is fluorescent by absorbing a light in a certain wavelength range, since this has a characteristic of looking like emitting light beautifully by the fluorescent luminous light being condensed at an end surface of formed shape, its use is not for passing/blocking light like the conventional optical filter but, for example, for use with design such as a slot machine, a name plate, a toy block, shelf for displaying goods or a DIY PC case.

Technical Solution

It is object of the present invention, which is accomplished by taking the above problem into consideration, to provide an optical filter and a lighting device using the same wherein the suppression of the melatonin secretion by the reception of light in the nighttime is prevented and the color of light is maintained desirable.

In order to achieve the above object of the invention, an optical filter in accordance with a first characteristic of the present invention has a mean transmissivity of a light beam in a wavelength range of about 480~550 nm about 30% or less.

When a light having a wavelength of about 464 nm is attenuated so as to set the prevention of the suppression of the melatonin secretion as a prime object as patent reference 2 (Japanese Patent Publication 2004-041545), it is difficult to maintain the color of the light desirable as described above. Therefore, as shown in FIGS. 1 and 4, the mean transmissivity of the light in the wavelength range of about 480~505 nm which has little effect on the isochromatic function and a high suppression efficiency of the melatonin secretion is set to be about 30% or less to solve the above problem.

FIGS. 7 through 10 are graphs illustrating a chromaticity coordinate transition when the transmissivity in the wavelength range of about 480~505 nm of a lamp having a relatively small amount of wavelength component which suppresses the melatonin secretion, a low color temperature and a high color rendition is varied from 100 to 0%. As shown in FIGS. 7 through 10, when the lamp or the transmissivity in this range is varied, the deviation Duv from the black body radiation locus is not changed.

In addition, actually when the light source is an incandescent color fluorescent lamp, the transmissivity of each wavelength component is varied to calculate a suppression luminous intensity efficiency of melatonin so that an absolute value of Duv is 5 or less. Here, the suppression luminous intensity efficiency of melatonin is calculated by an equation 1 below.

$$m = \frac{k_2 \int_{380}^{780} B(\lambda)S(\lambda)d\lambda \times k_1 \int_{380}^{780} V(\lambda)S_{white}(\lambda)d\lambda}{k_1 \int_{380}^{780} V(\lambda)S(\lambda)d\lambda \times k_2 \int_{380}^{780} B(\lambda)S_{white}(\lambda)d\lambda}$$ [Equation 1]

Where $B(\lambda)$ is the action spectrum of FIG. 1, $V(\lambda)$ is a standard luminous efficiency, $S(\lambda)$ is a spectral distribution of light after passing through an optical filter, $S_{white}(\lambda)$ is a spectral distribution of a base light source (in this case a incandescent color fluorescent lamp), and m is the suppression luminous intensity efficiency of melatonin.

In accordance with the suppression luminous intensity efficiency of melatonin (m) according to the equation 1, in case of the base light source, when melatonin is suppressed with E[1x], E/m[1x] is required. In order to prevent the suppression of the melatonin secretion which is one of the objects of the present invention, it is preferable that m is smaller than 1 and more preferably infinitely close to 0.

When the electric bulb color fluorescent lamp is used as the light source, FIG. 11 shows variation of the transmissivity with respect to the wavelength at which an absolute value of a Duv is 5 or less, a color temperature is 2600K or more, and a restraining illuminance efficiency of melatonin at the same illuminance is equal to or less than ½, also FIG. 12 shows variation of the transmissivity with respect to the wavelength at which an absolute value of a Duv is 5 or less, a color temperature is 2000K or more, and a restraining illuminance efficiency of melatonin at the same illuminance is equal to or less than ⅓. As shown in FIGS. 11 and 12, at least the mean transmissivity in the wavelength range of about 480~550 nm is about 30 or less so as to maintain the color as the lighting desirable and reduce the suppression of the melatonin secretion.

As described above, by setting the mean transmissivity in the wavelength range of about 480~550 nm having a relatively high suppression efficiency of melatonin which is about 30 or less, the present invention provides an effect of maintaining the color as the lighting desirable and reducing the suppression of the melatonin secretion. Therefore, a large amount of melatonin is secreted and a body temperature drop or sleep is accelerated.

In accordance with the optical filter of the first characteristic, an optical filter in accordance with a second characteristic of the present invention has a mean transmissivity in a wavelength range of about 430~445 nm is about 50% or less, and a mean transmissivity in a wavelength range of about 530~565 nm is between about 45% or more and about 75% or less.

Of the lamps having a low color temperature and high color rendition, a lamp that radiates light by mercury and a fluorescent substance such as a fluorescent lamp or an electrodeless fluorescent lamp has a unique luminous spectrum of mercury at about a wavelength of 435 nm as shown in FIG. 2. As shown in FIG. 1, the unique luminous spectrum of mercury has high suppression efficiency of the melatonin secretion. FIG. 13 is a graph illustrating a relative intensity of a spectral distribution of the incandescent color fluorescent lamp of FIG. 2 multiplied by the action spectrum of melatonin suppression and the isochromatic function of FIGS. 1 and 4.

As shown in FIG. 13, a light in a wavelength range of 430~445 nm has an equivalent suppression effect of melatonin as the wavelength range of 480~505 nm. However, contrary to the light having the wavelength range of 480~505 nm, this range simultaneously makes a large contribution on the isochromatic function $z(\lambda)$.

As shown in FIG. 11, in order to reduce the suppression effect of melatonin to a certain degree at the same illuminance (to ½ of melatonin suppression effect of the base incandescent color fluorescent lamp in the example of FIG. 11), it is not necessary to reduce the light in the wavelength range of 430~445 nm. However, as shown in FIG. 12, in order to further prevent the suppression of melatonin, the light in the wavelength range of about 430~445 nm is required to be 50 or less.

However, when the light in the wavelength range of 430~445 nm is reduced, the desired color cannot be maintained due to the large contribution to the isochromatic function $z(\lambda)$. FIG. 14 is a graph illustrating a chromaticity coordinate transition when energy in a wavelength ranges of 430~445 nm of the incandescent color fluorescent lamp is attenuated. As shown in FIG. 14, the light is green in color when the energy in this range is attenuated, and deviates farther (a plus direction when represented as Duv) from the black body radiation locus. Therefore, in order to reduce a green component, that is, a contribution to the isochromatic function $y(\lambda)$ to be closer to the black body radiation locus, the light in a wavelength range of 530~565 nm which makes a large contribution to the isochromatic function $y(\lambda)$ is reduced so that the color of the light has a natural color close to the black body radiation locus even when the light in the wavelength range of 430~445 nm is reduced. FIG. 15 is a graph illustrating a chromaticity coordinate transition when energy in a wavelength ranges of 530~565 nm of the incandescent color fluorescent lamp is attenuated. As shown in FIG. 15, when the energy in the wavelength range of 530~565 nm is attenuated, the chromaticity coordinate makes transition in a direction opposite to that of the black body radiation locus when the light in the wavelength range of 430~445 nm is attenuated (a minus direction when represented as Duv).

Therefore, a relation diagram wherein a transmissivity in the wavelength range of 530~565 nm of the incandescent color fluorescent lamp is varied so that the absolute value of the Duv is 5 or less when the transmissivity in the wavelength range of 430~445 nm of the incandescent color fluorescent lamp is 50% or less is shown in FIG. 16. As shown in FIG. 16, in order to further prevent the suppression of melatonin, when the transmissivity in the wavelength range of 430~445 nm of the incandescent color fluorescent lamp is 50% or less, a value of Duv becoming too large due to a reduction in the transmissivity in the wavelength range of 430~445 nm can be prevented by at least setting the transmissivity in the wavelength range of 530~565 nm to about 45% or more and about 75% or less, thereby maintaining the color of the light desirable.

As described above, of the lamps having a low color temperature and high color rendition, in case of a lamp that irradiates light by mercury and a fluorescent substance such as a fluorescent lamp or an electrodeless fluorescent lamp, when the transmissivity in a wavelength range of 430~445 nm is 50% or less, it has a effect of maintaining the color of the light desirable and further relieve the suppression of the melatonin secretion by setting the transmissivity in the wavelength range to 45% or more and about 75% or less. Therefore, a large amount of melatonin is secreted to accelerate a body temperature drop or sleep.

In order to embody the optical filter of the first and second characteristics, an optical filter in accordance with a third characteristic of the present invention is formed by molding (a) a transparent resin and (b) a resin composition material containing an orange color series florescent dye material.

In accordance with the optical filter of the third characteristic, an optical filter in accordance with a fourth characteristic of the present invention is formed by molding, (a) for 100 weight part of the transparent resin, (b) the resin composition material containing about 0.005~0.2 weight part of the orange color series florescent dye material.

In accordance with the optical filter of the third characteristic, an optical filter in accordance with a fifth characteristic of the present invention is formed by molding, (a) for 100 weight part of the transparent resin, (b) the resin composition material containing a compound of about 0.005~0.2 weight part of the orange color series florescent dye material and (c) about 0.25~4 weight part of an ultraviolet ray absorbent having an absorption peak at a wavelength ranging from 330 to 400 nm.

As shown in FIGS. 1 through 4, this has an object of maintaining the color of the light desirable and preventing the suppression of melatonin by reducing the transmissivity of the wavelength about 410 nm or less which has little effect on the isochromatic function.

In accordance with the optical filter of the third characteristic, an optical filter in accordance with a sixth characteristic of the present invention is formed by molding, (a) for 100 weight part of the transparent resin, (b) the resin composition material containing a compound of about 0.005~0.2 weight part of the orange color series florescent dye material and (b) about 0.005~0.01 weight part of a yellow color series florescent dye material.

On the other hand, a lighting apparatus of the present invention comprises an optical filter in accordance with the first through sixth characteristics.

DESCRIPTION OF DRAWINGS

FIG. 1 is an action spectrum of melatonin;

FIG. 2 is a graph illustrating a relative spectral distribution of various light sources;

FIG. 3 is a graph illustrating xy chromaticity;

FIG. 4 is a graph illustrating orange color function of, y and z;

FIG. 5 is graph illustrating a transmissivity of a yellow gelatin film;

FIG. 6 is a chromaticity coordinate graph when the filter in FIG. 5 is attached to an incandescent color fluorescent lamp and an incandescent lamp;

FIG. 7 is a graph illustrating a chromaticity transition regarding the incandescent color fluorescent lamp;

FIG. 8 is a graph illustrating a chromaticity transition regarding the incandescent lamp;

FIG. 9 is a graph illustrating a chromaticity transition regarding a high color rendition incandescent color fluorescent lamp;

FIG. 10 is a graph illustrating a chromaticity transition regarding a HID lamp;

FIG. 11 is a graph illustrating a transmissivity at which an absolute value of a Duv is 5 or less, a color temperature is 2600K or more, and a restraining illuminance efficiency of melatonin at the same illuminance is equal to or less than ½ by varying each wavelength component of the incandescent color fluorescent lamp;

FIG. 12 is a graph illustrating a transmissivity at which an absolute value of a Duv is 5 or less, a color temperature is 2000K or more, and a restraining illuminance efficiency of melatonin at the same illuminance is equal to or less than ⅓ by varying each wavelength component of the incandescent color fluorescent lamp;

FIG. 13 is a graph illustrating a relative intensity of a spectral distribution of the incandescent color fluorescent lamp multiplied by an orange color function or an action spectrum;

FIG. 14 is a graph illustrating a chromaticity transition when energy of a wavelength ranging from 430 to 445 nm of the incandescent color fluorescent lamp is attenuated;

FIG. 15 is a graph illustrating a chromaticity transition when energy of a wavelength ranging from 530 to 565 nm of the incandescent color fluorescent lamp is attenuated;

FIG. 16 is a relation diagram wherein a transmissivity of a wavelength ranging from 530 to 565 nm of the incandescent color fluorescent lamp is varied so that the absolute value of the Duv is 5 or less when a transmissivity of a wavelength ranging from 430 to 445 nm of the incandescent color fluorescent lamp is 50% or less;

FIG. 17 is a graph illustrating a transmissivity of an optical filter;

FIG. 18 is a graph illustrating a transmissivity of an optical filter formed by a transparent resin and an orange color series florescent dye material;

FIG. 19 is a graph illustrating a transmissivity of an optical filter;

FIG. 20 is a graph illustrating a transmissivity of an optical filter formed by a transparent resin, an orange color series florescent dye material and a yellow color series florescent dye material;

FIG. 21 illustrates various lighting apparatus;

FIG. 22 (A) through (C) are diagrams illustrating an enclosure configuration of the filter and (D) is a diagram illustrating a lighting apparatus overlapped with a diffusion plate;

FIG. 23 is a side view of a stand;

FIG. 24 is a perspective view illustrating a ceiling type lighting apparatus;

FIG. 25 is a perspective view illustrating a ceiling type lighting apparatus having a plurality of light sources;

FIG. 26 is a perspective view illustrating a down-light type lighting apparatus;

FIG. 27 is a perspective view illustrating a base-light;

FIG. 28 is a perspective view illustrating a straight tube lamp;

FIG. 29 (a) is a perspective view illustrating a sunglass, and (b) is a perspective view illustrating a goggle; and FIG. 30 is a perspective view illustrating a display.

BEST MODE

Of the optical filters used in the preferred embodiments, the optical filter in accordance with the first characteristic of the present invention consists of a transparent material having a spectrum characteristic shown in FIG. 17. This optical filter has at least a relatively high suppression efficiency of the melatonin secretion by light of a spectrum component corresponding to an output of a light source, and has a mean transmissivity in the wavelength range of about 480~505 nm which has little effect on a color the light about 30% or less. It is preferable that the transmissivity in the wavelength range is close to zero. However, because it is known that the suppression of the melatonin secretion and a dimension of action on a biorhythm are determined by an integral of (intensity of received light)×(time during which the light is received), the mean transmissivity about 30% or less has significance. In addition, in order to maintain the color of the light desirable, it is preferable that a transmissivity of a wavelength in other visible light range is as high as possible. However, it is not necessary for the transmissivity of the wavelength in other visible light range to be about 100 when the color of the light is maintained desirable.

FIG. 18 is a graph illustrating a transmissivity of an optical filter formed by a transparent resin and an orange color series florescent dye material. As shown in FIG. 18, the transmissivity in the wavelength range of 480~505 nm is effectively reduced by above-described configuration.

Of the optical filters used in the preferred embodiments, the optical filter in accordance with the second characteristic of the present invention consists of a transparent material having a spectrum characteristic shown in FIG. 19. This optical filter, in addition to the above-described spectrum characteristic, has a mean transmissivity at least in a wavelength range of about 430~445 nm of a spectrum component corresponding to an output of a light source being about 50% or less, and has a mean transmissivity in a wavelength range of about 530~565 nm being 45% or more and about 75% or less. Moreover, in order to prevent an effect on the color of the light, it is preferable that a transmissivity of a wavelength in other visible light range is as high as possible. However, it is not necessary for the transmissivity of the wavelength in other visible light range to be about 100% when the color of the light is maintained desirable. It is not necessary for the transmissivity in the wavelength range of 530~565 nm to be in the transmissivity range. For example, the wavelength range of 450~480 nm with a low transmissivity is tinted with green light in the way of reducing the transmissivity in the wavelength range of 430~445 nm. However, in this case, it is preferable that the mean transmissivity of the wavelength of 530~565 nm is slightly reduced to maintain the color of the light desirable. Although the suppression of melatonin can be prevented when the transmissivity in the wavelength range of 530~565 nm is reduced, this has a large effect on the isochromatic function $z(\lambda)$. Therefore, it is not desirable that the transmissivity in this range is reduced exceedingly.

FIG. 20 is a graph illustrating a transmissivity of an optical filter formed by a transparent resin, an orange color series florescent dye material and a yellow color series florescent dye material. As shown in FIG. 20, the transmissivity in the wavelength range of about 480~505 nm is effectively reduced by above-described configuration. In addition, when the mean transmissivity in the wavelength of about 430~445 nm is reduced only by increasing an amount of orange color series florescent dye material in a compound, the mean transmissivity of the wavelength of about 530~565 nm is also simultaneously reduced. Therefore, it is difficult to maintain a balance wherein the mean transmissivity of the wavelength of about 430~455 nm is maintained 50% or below and the mean transmissivity in the wavelength of about 530~565 nm is maintained about 45% and more and about 75% and less at the same time. Therefore, according to the mean transmissivity of the wavelength of about 530~565 nm by the orange color series florescent dye material, by the yellow color series florescent dye material, the mean transmissivity of the wavelength of about 430~445 nm is controlled to balance the transmissivity, and the suppressing of melatonin is further prevented when compared to the optical filter formed by molding only the transparent resin, the orange color series florescent dye material.

As a material for forming the optical filter in accordance with the present invention, (a) a transparent resin and (b) a resin composition material containing an orange color series florescent dye material may be used.

As an specific example of (a) component, an acrylic resin, a polystyrene resin, an AS resin, a vinyl chloride resin, a MS resin, a polycarbonate resin, an amorphous polyolefin resin, an AAS resin, an AES resin, an ABS resin, a polyethylenenaphthalate resin, a polyarylate resin, a polysulfone resin, a polyethersulfone resin, a polyetherimide resin, a polypropylene resin, a polyethylene resin, a polyamide resin, an EAV resin, a polylactic acid resin, a silicon resin, a fluorocarbon resin, a urethane resin, a unsaturated polyester resin or combinations thereof may be used. Of them, Acrylic series resin has good floodlighting, good endurance and wide usage, so it can be referred to desirable floodlighting resin. As an example of acrylic series resin of using for (a) component, it can be referred to ACRYPET VH (manufactured by MITSUBISHI RAYON CO., LTD.).

As the orange color series fluorescent dye material for (b) component, the fluorescent dye having a absorbing max wavelength rage about 515~560 nm can be used. Besides, as the orange color series fluorescent dye material, it is good that it has the absorbing wavelength rage about 470~510 nm and the absorbing wavelength range about 440~470 nm, or combinations thereof are good.

As an example of (b) component, any of well-known fluorescent dye material without limiting can be used, but it is desirable of using ferralyn series mixture.

As an example of the orange series fluorescent dye material for using as (b) component, it can be referred to PLAST ORANGE 8160 (manufactured by ARIMOTO CHEMICAL CO., LTD.).

In addition, it is desirable that the composition ratio of (a) component and (b) component is about 0.005~0.2 weight part per one hundred weight part of (a) component. When (b) component is too little, the mean transmissivity of light beam of the optical filter having wavelength about 480~505 nm goes to excess about 30%, so it don't prevent the melatonin suppression with maintaining optical color desirable. When (b) component is too much, the mean transmissivity of light beam of the optical filter having the rest of them is significantly reduced, so it is not desirable that the optical color temperature of light, after passing through optical filter when lamp is lightened, is over-reduced to the color temperature range written in the table 1 and 2 of JIS Z8752.

In addition, As an example of optical filter material for further preventing the suppression of melatonin without affecting the color of lighting, it can be referred to the resin composition containing UV absorbent having (c) absorbing peak of wavelength range about 330~400 nm and (b) the orange series fluorescent dye material within (a) floodlighting resin.

Here, As the composition ratio of (a) component, (b) component and (c) component, it is desirable that (b) component is about 0.005~0.2 weight part per hundred weight part of (a) component and (c) component is about 0.25~4 weight part per hundred weight part of (a) component. When (b) component is too little, the mean transmissivity of light bean of the optical filter having the wavelength range about 480~505 nm goes to excess about 30%, so it don't prevent the melatonin suppression with maintaining optical color desirable. When (b) component is too much, the mean transmissivity of light beam of the optical filter having about the rest of them is significantly reduced, so it is not desirable that the optical color temperature of light, after passing through optical filter when lamp is lightened, is over-reduced the color temperature range written in the table 1 and 2 of JIS Z8752. Besides, when (c) component is too little, it cannot reduce the transmissivity wavelength range about 410 nm and less that prevents the melatonin suppression without affecting with the color of light. When (c) component is too much, it prevents the melatonin suppression, but it is not desirable that it reduces the transmissivity of wavelength range about 410 nm and more, so it cannot maintain optical color desirable after passing through the optical filter.

As the kind of UV absorbent having absorbing peak of wavelength range about 330~400 nm of (c) component, it can be referred to benzotriazol series, benzophenone series and triazin series, etc. As the compound of them, any of well-known things without limiting can be used, but it is desirable to chlorobenzotriazol series or hydroxybenzophenone series from a point of view with effectively absorbing wavelength at 410 nm and less. As an example of them, it can be referred to 2-(2'-hydroxy-3'-t-buthyl-5'-methylphenyl)-5-chlorobenzotriazol, 2-(2'-hydroxy-3',5'-di-t-buthylphenyl)-5-chlorobenzotriazol, 2-(2'-hydroxy-4'-octoxyphenyl)benzotriazol, 2,2'-dihydroxy-4-methoxybenzophenon or 2,2'-dihydroxy-4,4'-dimethoxybenzophenon, 2,2',4,4'-tetrahydroxybenzophenon, or composition thereof can be used.

As an example of chlorobenzotriazol series UV absorbent for using as (c) component in market, it can be referred to TINUVIN 326 (manufactured by CHIBA SPECIALTY CHEMICAL K.K.). Besides, as an example of hydroxybenzophenone series UV absorbent, it can be referred to UVINUL 3050 (manufactured by BASF JAPAN LTD.)

In addition, As an example of optical filter material for further preventing the melatonin suppression without affecting with the color of light, it can be referred to resin composition having (b) the orange color series fluorescent dye material and (a) the yellow series dye material in (a) the floodlighting resin.

Here, As the composition ratio of (a) component, (b) component and (c) component, it is desirable that (b) component is about 0.005~0.2 weight part per hundred weight part of (a) component and (c) component is about 0.005~0.01 weight part per hundred weight part of (a) component. When (b) component is too little, the mean transmissivity of light beam of the optical filter having wavelength about 480~505 nm goes to excess about 30%, so it don't prevent the melatonin suppression with maintaining optical color desirable. When (b) component is too much, the transmissivity of light beam of the optical filter having about the rest of them is significantly reduced, so it is not desirable that the optical color temperature, after passing through optical filter when lamp is lightened, is over-reduced to the color temperature range written in the table 1 and 2 if JIS Z8752. Besides, When (d) component is too little, the mean transmissivity of light of wavelength range about 430~445 nm goes to excess about 50%, so it can not prevent the melatonin suppression with maintaining optical color desirable. When (d) component is too much, it can prevent the melatonin suppression, but it is not desirable that it miss the valance of the mean transmissivity of light of wavelength range about 430~445 nm and the mean transmissivity of light of wavelength range about 530~565 nm, so that it can not maintain optical color desirable after passing through the optical filter.

As the yellow series dye material of (d) component, commonly, organic pigment or inorganic pigment/dye are used. As the yellow inorganic dye, it is referred to Cd yellow, Cr yellow, Ti yellow (pigment yellow 53), Cr yellow (pigment brown 24) or Bengala yellow, etc. And, as the yellow organic dye, it is referred to condensate azoic series compound (pigment yellow 95), etc. So, any of well-known compounds can be used, but condensed azoic series compound (pigment yellow 95) is desirable.

As an example of the yellow series dye material for using as (d) component, it can be referred to CROMOPHTAL YELLOW GR (manufactured by CHIBA SPECIALTY CHEMICALS K.K.)

It related to the thickness of the optical filter that the orange series fluorescent dye material in (b) component, the UV absorbent having absorbing peak of wavelength range about 330~400 nm in (c) component and the concentration of the yellow series dye material in (d) component. When the thickness of the optical filter is heavy, reduce the concentration of (b), (c) and (d) component. In contrast, when the thickness of the optical filter is thin, raise the concentration of (b), (c) and (d) component. So, in the range of present invention, it can be set up freely.

In resin composition of using for the optical filter in present invention, as occasion demands, various well-known additives can be contained by well-known process in the range of not damaging capability. As an additive, it can be referred to that the coloring of dye and pigment, etc; The optical diffusing agent (There is surface-treated inorganic corpuscular) as the organic corpuscular of cross-linked styrene series corpuscular, cross-linked or polymer acryl series corpuscular, cross-linked styrene-acryl series corpuscular, cross-linked styrene-butadiene series corpuscular, cross-linked silicone corpuscular, cross-linked siloxane series corpuscular, cross-linked urethane series corpuscular and melamine series compound, etc, and inorganic corpuscular of Calcium Carbonate, Calcium Fluoride, Potassium Fluoride, Potassium phosphate, Zinc Oxide, Magnesium Sulfate, Barium Sulfate, Titanium dioxide, Titanic acid Potassium, Aluminum Hydroxide, Magnesium Hydroxide, Magnesium Carbonate, Alumina, Mica, Cerium oxide, Magnesium Stearate, Lithium Stearate, Calcium Stearate, Zinc Stearate, Barium Stearate, Crystal form Silica, Amorphous Silica, Glass Flake, Glass Fiber, Glass Bead, Clay and Talc, etc; The spreading agent or Dispersing agent for developing the dispersibility of pigment and optical diffusing agent; The high impact reforming agent known for rubber-phase polymer having main component as acrylate ester and methacrylate ester series; The heat-resisting stabling agent and the anti-weathering reforming agent as hindered amine series, hindered phenol series, benzoate series; The UV absorbing agent as Benzotriazol series, Benzophenone series, Triazine series, Malonic ester series, Salicylate series, Cyanoacrylate series and Oxanilide series; The flame retardant as ester phosphate; The lubricant as palmitic acid and stearyl alcohol; The Biocides of organic field and inorganic field; The antistatic agent; and The slipping agent. In addition, combinations thereof can be used.

The resin composition of using for optical filter in present invention, is achieved by sufficiently mixing floodlighting resin of (a) component with the orange color series fluorescent dye material of (b) component, and by dispersing equally in (a) component (like as composing of UV absorbent having absorbing peak of wavelength at 330~400 nm and the yellow series dye material of (d) component). But, when (a) component is solid, it is used by pallet-type. In example, the designated amounts of each component are mixed mechanically by mixing device as hensel mixer and tumbler. And, by using the extruder and banbery mixer having 1 axis/2 axis screw, it is mixed in melting state sufficiently in temperature of plasticizing and floating (a) component, and then it is manufactured by general well-known process as the process of fixing to pallet, etc.

A method for forming the optical filter of the present invention is not limited in particular. As a formation method, for example, injection molding, extrusion molding, blow molding, inflation molding, calender molding, compression molding, transfer molding, vacuum molding, pressured air molding, glass cast method, continuous casting method and molding method may be used, and the method can be selected according to a size, a shape, a thickness and the like of the optical filter.

These optical filters have various uses, for example a cover for lighting apparatuses such as a ceiling light, a pendant type light, a kitchen light, a bathroom light, a chandelier, a stand, a bracket, a kerosene lamp, a garage light, a eaves light, a doorpost light, a porch light, a garden light, a entrance light, a foot light, stairway light, a guidance light, an outdoor lamp, a down light, a base light, an electrical illumination signboard and a sign, a cover of a lighting apparatus for vehicle such as an automobile and a two-wheeled vehicle, and a cover of a lighting apparatus used in airplane or a Shinkansen car. In addition, the optical filter may be used for other than lighting apparatuses such as a lens portion of glasses, sunglasses or a goggle, or an optical filter for a television or a display.

A preferred embodiment of the present invention will now be described with reference to FIGS. 21 through 30. In addition, the present invention is not limited to the preferred embodiment.

The optical filter in accordance with present invention may be used for a lighting apparatus comprising a light source 1, an optical filter 2, a reflecting plate 3, a control unit and a power supply 4 as shown in FIG. 21. The optical filter 2 is disposed on a light-emitting surface of about an opposite side of the reflecting plate 3 having the light source 1 therebetween. Alternately, as shown in FIG. 21(B), the optical filter 2 is disposed on the light-emitting surface surrounding the light source 1 without the reflecting plate 3. The optical filter 2 is formed to be a plane or curved surface. In accordance with claims 3 through 6, the optical filter may be formed of the resin composition material and other means may be employed. In addition, the light source having a relatively low color temperature (for example, about 3000K or below) and a desirable color grade such as, but not limited to, a fluorescent lamp, an incandescent lamp, an electrodeless fluorescent lamp, HID lamp and the like is preferred.

Moreover, as shown in FIGS. 22(A) through (C), the optical filter 2 disposed at a light-emitting portion of the light source 1 may be accommodated inside the reflecting plate 3. That is, an optical filter enclosure unit 10 for accommodating the optical filter 2 is formed at the reflecting plate 3. A movement of the optical filter 2 is performed manually or automatically corresponding to the biorhythm of an object person.

As shown in FIG. 22(D), a diffusing plate 12 such as a milky white plate or a prism may be disposed at an outer side of the optical filter.

FIG. 23 illustrates an applied example of a stand type apparatus. The optical filter 2 may be attached to a floor stand as shown in FIG. 23, and the apparatus may be installed in a living room or a bedroom to provide light to the living room without preventing the secretion of melatonin in the nighttime. The optical filter 2 may be attached to a study stand for use with a work or study in the nighttime to provide a light necessary for the work or study without preventing the secretion of melatonin in the nighttime. Moreover, the optical filter 2 may be attached to a bedside stand to be used as a reading light prior to sleep. In addition, as shown in FIG. 22, it is preferable that the optical filter 2 of the present invention is designed to be detachable, and the diffusing plate 12 such as the milky white plate or the prism may be disposed at the farther outer side of the optical filter 2.

FIG. 24 illustrates an example wherein the optical filter 2 is attached as a globe of a ceiling type lighting apparatus. By installing ceiling type lighting apparatus in the living room or the bedroom, the necessary light may be provided without preventing the secretion of melatonin in the nighttime. That is, as shown in FIG. 24-A, a globe portion may be formed with the optical filter 2. In addition, as shown in FIG. 22, the optical filter 2 of the present invention may be detachable, and the diffusing plate 12 such as the milky white plate or the prism may be disposed at the farther outer side of the optical filter 2. As shown in FIG. 24-B, the optical filter 2 may be attached along a circumference of the light source 1, and the globe 13 may be individually installed. The lamp includes but not limited to a fluorescent lamp, an electrodeless fluorescent lamp, incandescent lamp and the like. The light source 1 may have a low color temperature such as an incandescent lamp color.

FIG. 25 illustrates an example lighting apparatus wherein two or more light sources 14 and 15 are covered by a milky white or transparent globe 13 and the optical filter 2 of the present invention is attached to the globe 13 corresponding to one light source 15. In accordance with the example, by researching a disposition of the optical filter 2 wherein the optical filter 2 optically filters a light from at least one light source 15 of the two or more light sources 14 and 15, the light source 14 is used during the daytime by for example setting the light source 14 to which the optical filter 2 is not attached to white in color and the light source 15 is used during the nighttime by for example setting the light source 15 to which the optical filter 2 is attached to the light source 15 having a low color temperature such as an incandescent color to provide a light. In addition, for example, by setting the light source 14 to which the optical filter 2 is not attached to have a high output and a high color temperature, as disclosed in patent reference 3 (Japanese patent application no. 2004-128465), the biorhythm may be effectively adjusted using the light source having the high color temperature during the morning, the light may be configured to be white in color by mixing both lights during the afternoon, and light may be provided from the light source which as the optical filter of the present invention attached thereto during the nighttime. Moreover, in accordance with this example, as shown in FIG. 22, the optical filter 2 of the present invention may also be detachable, and the diffusing plate 12 such as the milky white plate or the prism may also be disposed at the farther outer side of the optical filter 2. As shown in FIG. 24-B, the optical filter 2 may be attached along circumferences of the light sources 14 and 15, and the globe 13 may be individually installed. The light source 14 may include a white color light source and the light source 15 may include an incandescent color light source having a low color temperature.

FIG. 26 illustrates an example wherein the optical filter 2 of the present invention is attached to a down-light type lighting apparatus. In addition, the optical filter of the present invention may also be attached to a bracket-type apparatus. As shown in FIG. 22, the optical filter 2 of the present invention may be detachable, and the diffusing plate such as the milky white plate or the prism 12 may also be disposed at the farther outer side of the optical filter 2. The lamp includes but not limited to a fluorescent lamp, an electrodeless fluorescent lamp, incandescent lamp and the like.

FIG. 27 illustrates an example wherein the optical filter 2 of the present invention is attached to a base-light 18 installed in an office or a hospital. As shown in FIG. 27, when the apparatus is a multiple lamp type, the optical filter 2 may be attached to a portion of the light sources to optically filter a light and change according to a time zone as disclosed in patent reference 3 or the optical filter 2 may be attached to the entire light sources. As shown in FIG. 22, the optical filter 2 of the present invention may be detachable, and the diffusing plate such as the milky white plate or the prism 12 may also be disposed at the farther outer side of the optical filter 2. The lamp is not particularly limited as is in the FIG. 26.

FIG. 28 illustrates a case wherein a light source is directly covered by the filter of the present invention. The filter may be attached directly to the light source 17, or as shown in FIG. 28 A, have a cylinder shape for a facile exchange and detachment. As shown in FIG. 28 B, it is allowed that the filter is partly opened without covering the entire circumference of the light source 17. In addition, the shape of a lamp is not shape-dependent and not limited to a strait type, but may include a bulb shape as shown in FIG. 28 C or a circular shape as shown in FIG. 28 D and the like, and the lamp may be covered by the optical filter 2 of the present invention. As shown in FIG. 28, the filter may cover or be directly attached (attached with an adhesive) to the light source. The lamp is not particularly limited as is in the FIG. 26.

FIG. 29 (a) illustrates an example other than an application for the above-described lighting apparatus, wherein the optical filter 2 of the present invention is attached to a sunglass 20 of FIG. 29(a) or a goggle 21 of FIG. 29(b). By attaching the filter to the sunglass 20 or the goggle 21, a light that suppresses melatonin may be reduced regardless of surrounding lighting environment.

FIG. 30 illustrates an example wherein the optical filter 2 of the present invention is attached to a television or a display 22 of a PC. Because the display is self-luminous, watching television or performing a VDT work in the nighttime concerns the suppression of the melatonin secretion. Therefore, attaching the optical filter 2 of the present invention may prevent that phenomenon.

MODE FOR INVENTION

Embodiment

A preferred embodiment of the present invention will now be described in more detail. However, the present invention is not limited to the embodiment.

(a) A transparent resin and (b) a resin composition material containing an orange color series florescent dye material are compounded using a tumbler (the same method is performed when simultaneously compounding (b) an ultraviolet ray absorbent (c) a yellow color series florescent dye). These materials were roll mixing milled and melted using a rotating biaxial extruding machine in the same direction of a 47 mm in cylinder diameter and L/D 31.5 under a temperature of 230° C. and then water-cooled by a strand bus and pellet is obtained by cutting by a cutter. Thereafter, the pellet is melted using a uniaxial extruding machine of a 47 mm in cylinder diameter under a temperature of 240° C. and extruded fro a T-die to obtain a sheet 400 mm wide and 1.0 mm thick. The sheet is then cut Φ300 mm in size to obtain a lighting cover for a stand.

ACRYPET VH0001 (which is a brand name of acryl series resin manufactured by MITSUBISHI RAYON CO., LTD.) is used in floodlighting resin of (a) component, PLAST ORANGE 8160 (which is a brand name of ferralyn series compound manufactured by ARIMOTO CHEMICAL CO., LTD.) is used in the orange series fluorescent dye material of (b) component, TINUVIN 326 (which is a brand name of chlorobenzotriazol series UV absorbent manufactured by CHIBA SPECIALTY CHEMICALS K.K.) and UVINUL 3050 (which is a brand name of hydroxybenzophenone series UV absorbent manufactured by BASF JAPAN LTD. The manufactured goods name of) are used in UV absorbent having absorbing peak of wavelength rage of 330~400 nm in (c) component, and CROMOPHTAL YELLOW GR (which is a brand name of condensed azoic series compound manufactured by CHOIBA SPECIALTY CHEMICALS K.K.) is used in the yellow series dye material in (d) component.

In embodiment, the way to test and value is described in below.

[1] The mean value of transmissivity of all light beams having wavelength range of 480~505 nm It was measured in every 5 nm gap by magnetic spectrophotometer as U-4000 from The HITACHI. And, The objecting data was the mean value of transmissivity of wavelength range of 480~505 nm.

[2] Duv

The optical filter is installed to the light apparatus (e.g. the manufactured goods of SC350 by MATSUSITA ELECTRIC WORKS, LTD.) in market, and the light source is taken as incandescent color fluorescent lamp (e.g. the manufactured goods of twin Pa40W by MATSUSHITA ELECTRIC INDUSTRIAL LIGHTING COMPANY). The spectral distribution of luminous light is measured by the spectrum detector of PMA-11 by HAMAMATSU PHOTONICS K.K. So, the Duv is obtained based on JIS Z8725 and the measured value above, and each value is indexed by ⊚, ○, Δ and X. the valuing standard, is that ⊚ means below ±1, ○ means below ±3, Δ means between ±3 and ±5 and X means over ±5 or incapable of measuring.

[3] The correlation color temperature

As the way of [2] process described above, measuring the spectrum distribution of luminous light, and based on JIS Z8725, the value measuring of correlation color temperature above is taken to the objecting value. Besides, when the correlation color temperature is under 1560K, valuing too low as the correlation color temperature of light from Tag 1 or 2 in JIS Z8725, and it writes '<1560'. So, it cannot measure the item for measurement [2] Duv and [4] The mean color rendition-valuing index.

[4] The mean color rendition valuation index

As the way of [2] described above, measuring the spectral distribution of luminous light, the mean color rendition valuation index is maintained based on JIS Z8726, and the index measured above is taken as the objecting index.

[5] The suppression luminous intensity efficiency of melatonin

As the way of [2] described above, measuring the spectral distribution of transmitted light, taking action spectrum in FIG. 1 as B(λ), taking the standard luminous efficiency as V(λ), taking the spectral distribution of transmitting light after passing through the optical filter as S(λ) and it is taken the spectral distribution of base light source(incandescent color fluorescent lamp in this occasion) as $S_{white}(λ)$. And as described below, by Equation 1, the suppression luminous intensity efficiency of melatonin is calculated.

By the Equation, The suppression luminous intensity efficiency of melatonin, in case that the melatonin secretion is suppressed by E[1x] in base light source, needs E/m[1x] in order to suppress the melatonin secretion as same effect as above in the transmitted light after passing through the optical filter. One of object in present invention is to prevent the suppressing of melatonin secretion, so it becomes less than 1, it becomes close to 0 desirably. So, it is valued by valuing standard described below.

The valuing standard is that ○ is under 0.5, Δ is from 0.5 and more to 0.75 and X is 0.75 and more.

[6] The effect of the suppression luminous intensity efficiency of melatonin in composition of (c) component and (d) component The object of (c) component or (d) component is to prevent the suppressing of melatonin, and to maintain light color desirable by composing (c) component and (d) component. Therefore, it is valued how the effect of the illuminance efficiency of suppressing melatonin is reduced lower in the composition of (c) component or (d) component by basis described below than the composition of only (a) component and (b) component.

The valuing standard is that ○ means lower effect of the illuminance efficiency of suppressing melatonin than that of the mixing same amount of (a) component and (b) component, respectively with only (a) component and (b) component, and X means equal to and higher effect of the illuminance efficiency of suppressing melatonin than that of the same amount of (a) component and (b) component, respectively with only (a) component and (b) component.

The embodiment and comparative example of present invention in tables 1 and 2

TABLE 1

EMBODIMENTS AND EVALUATING RESULTS THEREOF

|  |  | Embodiment 1 | Embodiment 2 | Embodiment 3 | Embodiment 4 |
|---|---|---|---|---|---|
| Composition (Weight part) | (a) Acryl Series resin | 100 | 100 | 100 | 100 |
|  | (b) Ferralyn Series compound | 0.03 | 0.03 | 0.03 | 0.03 |
|  | (c) Chlorobenzotriazol Series or hydroxybenzophenone series compound | — | 1 | — | 0.3 |
|  | (d) Condensed azoic series compound | — | — | 0.005 | 0.005 |
| Evaluation | [1] Transmissivity [%] at 480~505 nm | 11.6 | 11.6 | 11.2 | 11.2 |
|  | [2] Duv | ◎ | ◎ | ◎ | ◎ |
|  | [3] Color Temperature [K] | 2120 | 2120 | 2090 | 2090 |
|  | [4] The mean color rendition valuation index | 65 | 65 | 66 | 66 |
|  | [5] The suppression luminous intensity efficiency of melatonin | ○ | ○ | ○ | ○ |
|  | [6] The effect of the suppression luminous intensity efficiency of melatonin in composition of (c) component and (d) component | — | ○ | ○ | ○ |

TABLE 2

COMPARATIVE EXAMPLES

|  |  | Comparative example 1 | Comparative example 2 | Comparative example 3 | Comparative example 4 | Comparative example 5 | Comparative example 6 | Comparative example 7 |
|---|---|---|---|---|---|---|---|---|
| Composition (Weight part) | (a) Acryl Series resin | 100 | 100 | 100 | 100 | 100 | 100 | 100 |
|  | (b) Ferralyn Series compound | 0.03 | 0.3 | 0.03 | 0.03 | 0.03 | 0.03 | — |
|  | (c) Shlorobenzotriazol Series or hydroxybenzophenone series compound | — | — | 0.006 | 8 | — | — | — |
|  | (d) Condensed azoic series compound | — | — | — | — | 0.001 | 0.02 | — |
| Evaluation | [1] Transmissivity [%] at 480~505 nm | 71.7 | 4.3 | 11.6 | 11.6 | 11.6 | 11.6 | 92 |

TABLE 2-continued

COMPARATIVE EXAMPLES

|  | Comparative example 1 | Comparative example 2 | Comparative example 3 | Comparative example 4 | Comparative example 5 | Comparative example 6 | Comparative example 7 |
|---|---|---|---|---|---|---|---|
| [2] Duv | ⊚ | X | ⊚ | Δ | ⊚ | X | ○ |
| [3] Color Temperature [K] | 2120 | <1560 | 2100 | 2110 | 2120 | <1560 | 3200 |
| [4] The mean color rendition valuation index | 78 | — | 65 | 65 | 65 | — | 84 |
| [5] The suppression luminous intensity efficiency of melatonin | Δ | ○ | ○ | ○ | ○ | ○ | X |
| [6] The effect of the suppression luminous intensity efficiency of melatonin in composition of (c) component and (d) component | — | — | X | ○ | X | ○ | — |

INDUSTRIAL APPLICABILITY

In accordance with the optical filter of the first characteristic of the present invention, as shown in FIGS. 1 and 4, the mean transmissivity in the wavelength range of about 480~505 nm which has high suppression efficiency of the melatonin secretion in the nighttime is set to be about 30% or less to provide a effect of maintaining the color of light desirable and relieving the suppression of the melatonin secretion. Therefore, a large amount of melatonin is secreted and a body temperature drop or sleep is accelerated. In addition, of the lamps having a low color temperature and high color rendition, a lamp that radiates light by mercury and a fluorescent substance such as a fluorescent lamp or an electrodeless fluorescent lamp has a unique luminous spectrum of mercury about a wavelength of 435 nm as shown in FIG. 2. As shown in FIG. 13, this unique luminous spectrum of mercury has high suppression efficiency of the melatonin secretion. However, because this range simultaneously has a much contribution to the isochromatic function $z(\lambda)$ as shown in FIG. 4, the desirable color of lighting cannot be maintained due to Duv becoming large when the transmissivity in this wavelength range is reduced.

Therefore, in accordance with the optical filter of the first characteristic, an optical filter in accordance with a second characteristic of the present invention has a mean transmissivity in a wavelength range of about 430~445 nm is about 50% or less, and a mean transmissivity in a wavelength range of about 530~565 nm is about 45% or more and about 75% or less to provide a effect of maintaining the color of the light desirable and also relieving the suppression of the melatonin secretion. Therefore, a large amount of melatonin is secreted and a body temperature drop or sleep is accelerated.

In addition, as a mean for embodying the above-described optical filter, the optical filter in accordance with a third characteristic of the present invention is formed by molding (a) a transparent resin and (b) a resin composition material containing an orange color series florescent dye material to embody the optical filters in accordance with the first and second characteristics.

The optical filter in accordance with a fourth characteristic of the present invention is formed by molding, (a) for 100 weight part of the transparent resin, (b) the resin composition material containing about 0.005~0.2 weight part of the orange color series florescent dye material to embody the optical filters in accordance with the first and second characteristics.

The optical filter in accordance with a fifth characteristic of the present invention is formed by molding, (a) for 100 weight part of the transparent resin, (b) the resin composition material containing a compound of about 0.005~0.2 weight part of the orange color series florescent dye material and (c) about 0.25~4 weight part of an ultraviolet ray absorbent having an absorption peak at a wavelength ranging from 330 to 400 nm to embody the optical filter in accordance with the third characteristic of the present invention. The suppression of melatonin can be prevented further than the optical filter in accordance with the third characteristic of the present invention without altering the color of the light.

The optical filter in accordance with a sixth characteristic of the present invention is formed by molding, (a) for 100 weight part of the transparent resin, (b) the resin composition material containing a compound of about 0.005~0.2 weight part of the orange color series florescent dye material and (b) about 0.005~0.01 weight part of a yellow color series florescent dye to embody the optical filter in accordance with the second characteristic of the present invention more easily.

In accordance with the lighting apparatus of the present invention, the lighting apparatus comprises an optical filter in accordance with the first through sixth characteristics to secrete a large amount of melatonin thereby accelerating a body temperature drop or sleep.

The invention claimed is:
1. An optical filter, the optical filter comprising:
an optical filter means for preventing melatonin suppression,
wherein a mean transmissivity of the optical filter for light having a wavelength of about 480-505 nm passing through the optical filter is about 30% or less,
wherein a mean transmissivity of the optical filter for light having a wavelength of about 380-440 nm passing through the optical filter is about 50% or more,
wherein a mean transmissivity of the optical filter for light having a wavelength of about 430-445 nm passing through the optical filter is about 50% or less,
wherein a mean transmissivity of the optical filter for light having a wavelength of about 530-565 nm passing through the optical filter is between about 45% and about 75%, and
wherein a mean transmissivity in a wavelength range of about 400-440 nm is greater than about 30%.
2. The optical filter in accordance with claim 1, wherein the optical filter means is formed by molding a transparent resin and a resin composition material containing an orange color series fluorescent dye material.

3. The optical filter in accordance with claim 2, wherein, for 100 weight part of the transparent resin, the resin composition material containing about 0.005-0.2 weight part of the orange color series fluorescent dye material is molded.

4. The optical filter in accordance with claim 2, wherein, for 100 weight part of the transparent resin, the resin composition material containing a compound of about 0.005-0.2 weight part of the orange color series fluorescent dye material and about 0.25-4 weight part of an ultraviolet ray absorbent material having an absorption peak at a wavelength ranging from 330 to 400 nm is molded.

5. The optical filter in accordance with claim 2, wherein, for 100 weight part of the transparent resin, the resin composition material containing a compound of about 0.005-0.2 weight part of the orange color series fluorescent dye material and about 0.005-0.01 weight part of a yellow color series florescent dye material is molded.

6. A lighting apparatus having an optical filter in accordance with claim 1.

* * * * *